(12) United States Patent
Izumi et al.

(10) Patent No.: US 11,119,033 B2
(45) Date of Patent: Sep. 14, 2021

(54) CONFORMATION ANALYSIS DEVICE, ANALYSIS METHOD, CONFORMATIONAL NOTATION DEVICE AND NOTATION METHOD

(75) Inventors: Hiroshi Izumi, Ibaraki (JP); Atsushi Ogata, Ibaraki (JP); Kazuyuki Takeo, Ibaraki (JP); Hideki Kobayashi, Ibaraki (JP)

(73) Assignee: Hiroshi Izumi, Tsukuba (JP)

( * ) Notice: Subject to any disclaimer, the term of this patent is extended or adjusted under 35 U.S.C. 154(b) by 1120 days.

(21) Appl. No.: 12/385,856

(22) Filed: Apr. 22, 2009

(65) Prior Publication Data

US 2009/0248321 A1 Oct. 1, 2009

Related U.S. Application Data

(63) Continuation-in-part of application No. PCT/JP2008/051673, filed on Feb. 1, 2008.

(30) Foreign Application Priority Data

Mar. 23, 2007 (JP) .............................. JP2007-077133
Apr. 24, 2008 (JP) .............................. JP2008-113263

(51) Int. Cl.
*G16C 10/00* (2019.01)
*G01N 21/19* (2006.01)

(52) U.S. Cl.
CPC .............. *G01N 21/19* (2013.01); *G16C 10/00* (2019.02); *G01N 2201/129* (2013.01)

(58) Field of Classification Search
None
See application file for complete search history.

(56) References Cited

FOREIGN PATENT DOCUMENTS

| JP | 2005-91050 | 4/2005 |
| JP | 2005-91164 | 4/2005 |
| JP | 2005-345131 | 12/2005 |

OTHER PUBLICATIONS

International Search Report dated Apr. 15, 2008 for International Application No. PCT/JP2008/051673.

(Continued)

*Primary Examiner* — Karlheinz R. Skowronek
(74) *Attorney, Agent, or Firm* — Wenderoth, Lind & Ponack, L.L.P.

(57) ABSTRACT

A conformation analysis device and analysis method with which discrimination can be achieved even if there is a subtle difference in a conformational structure, a given molecule can be processed in a unified manner, and large-scale computer processing can be performed, and a conformational notation device and notation method with which even in the case where a conformation cannot be uniquely determined if a rule in accordance with the IUPAC Nomenclature is followed, the conformation can be uniquely notated, a given molecule can be processed in a unified manner, and large-scale computer processing can be performed, are provided. In one embodiment of the invention, a processing section receives an input of a chemical structural formula of a compound to be analyzed, puts a predetermined code indicating a dihedral angle to each chemical binding site based on the received chemical structural formula, extracts an encoded conformational notation of interest with respect to a structure capable of uniquely determining a conformation with one conformational notation, and stores the extracted encoded conformational notation in a storage section. Then, the processing section creates a molecular model based on the extracted encoded conformational notation, performs geometry optimization and frequency calculation for the created molecular model, determines a geometry optimized structure and a physical (Continued)

property value of the geometry optimized structure, extracts the encoded conformational notation from the storage section, and performs a homology analysis based on the notation.

8 Claims, 10 Drawing Sheets

(56) References Cited

OTHER PUBLICATIONS

Ana A. Alcaraz et al., "The T-Taxol Conformation", J. Med. Chem., No. 49, Mar. 24, 2006, pp. 2478-2488.

Hiroshi Izumi et al., "Direct Observation of Odd-Even Effect for Chiral Alkyl Alcohols in Solution Using Vibrational Circular Dichroism Spectroscopy", J. Am. Chem. Soc., No. 126, Dec. 13, 2003, pp. 194-198.

Hiroshi Izumi et al., "Fliplike Motion in the Thalidomide Dimer: Conformational Analysis of (R)-Thalidomide Using Vibrational Circular Dichroism Spectrocopy", J. Org. Chem., No. 72, Dec. 7, 2006, pp. 277-279.

Hiroshi Izumi et al., "Vibrational Circular Dichroism Analysis Reveals a Conformational Change of the Baccatin III Ring of Paclitaxel: Visualization of Conformations Using a New Code for Structure—Activity Relationships", J. Org. Chem., No. 73, Feb. 15, 2008, pp. 2367-2372.

Zhi-Xiang Wang et al., "Strike a Balance: Optimization of Backbone Torsion Parameters of AMBER Polarizable Force Field for Simulations of Proteins and Peptides", J. Comput. Chem., No. 27, 2006, pp. 781-790.

Izumi et al. "Data Mining of Supersecondary Structure Homology between Light Chains of Immunoglobins and MHC Molecules: Absence of the Common Conformational Fragment in the Human IgM Rheumatoid Factor," J. Chem. Inf. Model., vol. 53, pp. 583-591, Feb. 2013.

Izumi et al. "Structural analysis using the program of conformation code for organic molecules (CCOM)," Proceedings of 38th Symposium on Chemoinformatics, pp. 22 and 23, Oct. 2015.

Izumi et al. "Three-Dimensional Chemical Structure Search Using the Conformational Code for Organic Molecules (CCOM) Program," Chirality, vol. 28, Issue 5, pp. 370-375, May 2016.

Hiroshi Izumi, "Development of Conformational Code for Organic Molecules (CCOM) Program for the Input of Artificial Intelligence," Abstract of the 97th Annual Meeting of the Chemical Society of Japan, 1PC-140, 2017.

Izumi, H. "Consideration of the sequence rule in rule P-94.2", Chemistry International, vol. 40, Issue 3, 2018, pp. 36-37.

Izumi, H. "Homology Searches Using Supersecondary Structure Code", Protein Supersecondary Structures, 2nd ed., A. E. Kister (Ed.), Springer, Berlin, (2019, in press) 23 pages.

bacc233153tail+4322324
Paclitaxel tail+4322324
Paclitaxel tail methyl ester ibu-32ατ(ph-3τ5β)   ibu-32αα(ph-3α5β)

levo-2-15(pipa-11α)   levo-2-15(pipa-11β)

CONFORMATION ANALYSIS DEVICE, ANALYSIS METHOD, CONFORMATIONAL NOTATION DEVICE AND NOTATION METHOD

CROSS-REFERENCE TO RELATED APPLICATION

This application is a continuation-in-part of International Application No. PCT/JP2008/051673, filed Feb. 1, 2008, which claims priority to Japanese Patent Application No. 2007-077133, filed Mar. 23, 2007, the entire contents of each of these applications being incorporated herein by reference in their entirety.

Also this application claims priority to Japanese Patent Application No. 2008-113263, filed Apr. 24, 2008, the entire contents of the application being incorporated herein by reference in their entirety.

BACKGROUND OF THE INVENTION

Field of the Invention

The present invention relates to a device and a method for simply and more precisely analyzing conformations of pharmaceutically active species and the like related to drug actions and the like.

Also, the present invention relates to a device and a method for simply and more precisely notating a physical property value related to a drug action and the like along with a conformational structure thereof.

As the structures of various proteins have been revealed with the progress of post-genomic studies, it has been revealed that, for example, Taxol (paclitaxel) which functions as an anticancer agent is stabilized by binding to a protein called tubulin which constitutes microtubules to inhibit depolymerization of tubulin thereby inhibiting cancer cell division. Further, in an environment where a drug functions, the drug is in a liquid phase state, therefore, for example, Taxol can have various forms, and the structure of the active species thereof draws interest from the viewpoint of structure-activity relationship. These various forms are called conformations, and the conformations of various active species of Taxol have been proposed and discussed (Non-patent document 1). However, due to the restriction of spatial resolution of existing devices, restriction of NMR time scale specific to nuclear magnetic resonance (NMR) devices, problems of accuracy of molecular force field calculation and the like, there has been an interest in how such conformations of the active species are notated. For example, at present, notations such as T-Taxol and PTX-NY have been used for Taxol, however, it is impossible to compare the conformations based on these notations themselves.

As for genomes, by notating them using simplified symbols of G, C, T and A in common, it has become possible to perform large-scale computer processing and remarkable progress has been accomplished.

The present inventors have found that vibrational circular dichroism (VCD) bands of substances having chirality such as biomolecules are extremely sensitive to conformations (Non-patent documents 2 to 4), and have already made a proposal regarding a novel structural analysis method utilizing the VCD spectroscopy (Patent documents 1 and 2). In the documents, a proposal has been made that conformations are notated using simplified symbols. However, it had a problem that when there is a subtle difference in the structure, discrimination cannot be achieved.

The activity of a drug is considered to be dependent on a physical property attributable to a molecular conformation and a property involved in metabolism. The conformational structure of the above-mentioned active species has attracted attention from the viewpoint of structure-activity relationship for designing novel drugs, however, by a conventional method for notating molecular conformations by an orthogonal coordinate system or ZMATRIX, conformational structures cannot be simply notated, and therefore, simple notations such as T-Taxol and PTX-NY unique to individual conformations have been required. However, even with such simple notations, the individual conformations cannot be easily compared, and thus, a notation method which enables large-scale computer processing and facilitates comparison of conformations, and an analysis technique using the notation method have been demanded.

Also, the present inventors have found that vibrational circular dichroism (VCD) bands of substances having chirality such as biomolecules are extremely sensitive to conformations (Non-patent documents 2 to 4), and have already made a proposal required for a conformation analysis regarding conformation analysis device and analysis method incorporating a rule in accordance with the IUPAC Nomenclature which establishes that a conformation is notated based on a torsion angle formed by ligands which are bound to the respective ends of chemical bonds of interest and selected in accordance with a priority rule (Patent document 3). In the document, they have proposed that a notation is made using a simple encoded conformational notation with which even if there is a subtle difference in a conformational structure, comparison of the conformational structure can be easily performed using a simplified symbol, a given molecule can be processed in a unified manner, and large-scale computer processing can be performed, however, they have found that there is a problem that in the case of levofloxacin, ibuprofen or the like, when the rule in accordance with the IUPAC Nomenclature is followed, discrimination cannot be achieved if there is a more subtle difference in the structure. Further, as a priority rule for ligands of the IUPAC Nomenclature, in the case (3) where a ligand which provides the smallest torsion angle is selected when all ligands are the same, there may be a case where a plurality of molecular models correspond to one encoded conformational notation and a case where one molecular model can be expressed in a plurality of encoded conformational notations, and therefore, it was found that a conformation cannot be uniquely determined when the rule in accordance with the IUPAC Nomenclature is followed in some cases.

Therefore, in order to solve these problems, a notation technique for performing computer processing of a conformational structure has been demanded.

Non-patent document 1: A. A. Alcaraz et al., J. Med. Chem., 2006, 49, 2478

Non-patent document 2: H. Izumi et al., J. Am. Chem. Soc., 2004, 126, 194

Non-patent document 3: H. Izumi et al., J. Org. Chem., 2007, 72, 277

Non-patent Document 4: H. Izumi et al., J. Org. Chem., 2008, 73, 2367

Patent document 1: JP-A-2005-91050

Patent document 2: JP-A-2005-91164

Patent Document 3: PCT/JP 2008/051673

SUMMARY OF THE INVENTION

The present invention has been made in view of such circumstances of the prior art and has an object to provide conformation analysis device and analysis method with which discrimination can be achieved even if there is a subtle difference in a conformational structure, a given molecule can be processed in a unified manner, and large-scale computer processing can be performed.

Also, the present invention has an object to provide conformational notation device and notation method with which even in the case where a conformation cannot be uniquely determined if a rule in accordance with the IUPAC Nomenclature is followed, the conformation can be uniquely notated, a given molecule can be processed in a unified manner, and large-scale computer processing can be performed.

In order to achieve the above object, the present invention firstly provides a conformation analysis method characterized in that a processing section receives an input of a chemical structural formula of a compound to be analyzed; the processing section puts a predetermined code indicating a dihedral angle to each chemical binding site based on the received chemical structural formula, extracts an encoded conformational notation of interest with respect to a structure capable of uniquely determining a conformation with one conformational notation and stores the extracted encoded conformational notation in a storage section; the processing section creates a molecular model based on the extracted encoded conformational notation; the processing section performs geometry optimization and frequency calculation for the created molecular model and determines a geometry optimized structure and a physical property value of the geometry optimized structure; and the processing section extracts the encoded conformational notation from the storage section and performs a homology analysis based on the notation.

Further, the invention secondly provides a conformation analysis method characterized in that in the above method, the compound to be analyzed is an optically active molecule and a conformational structure of the optically active molecule in a liquid phase is verified by comparing an observed vibrational circular dichroism spectrum with a predicted spectrum obtained from candidate conformations.

Further, the invention thirdly provides a conformation analysis method characterized in that in the above method, as a method for indicating the dihedral angle, a rule in accordance with the IUPAC Notation is included.

Further, the invention fourthly provides a conformation analysis device characterized by comprising: a unit which receives an input of a chemical structural formula of a compound to be analyzed; a unit which puts a predetermined code indicating a dihedral angle to each chemical binding site based on the received chemical structural formula, extracts an encoded conformational notation of interest with respect to a structure capable of uniquely determining a conformation with one conformational notation and stores the extracted encoded conformational notation in a storage unit; a unit which creates a molecular model based on the extracted encoded conformational notation; a unit which performs geometry optimization and frequency calculation for the created molecular model and determines a geometry optimized structure and a physical property value of the geometry optimized structure; and a unit which extracts the encoded conformational notation from the storage unit and performs a homology analysis based on the notation.

Further, the invention fifthly provides a conformation analysis device characterized in that in the above device, in the case where the compound to be analyzed is an optically active molecule, the device further comprises a unit which compares an observed vibrational circular dichroism spectrum with a predicted spectrum obtained from candidate conformations and verifies a conformational structure of the optically active molecule in a liquid phase.

Further, the invention sixthly provides a conformation analysis device characterized in that in the above device, as a method for indicating the dihedral angle, a rule in accordance with the IUPAC Notation is included.

According to the present invention, a conformation is analyzed using a method for notating a molecular conformation by encoding a position of a chemical bond and a dihedral angle therefor, and therefore, discrimination can be achieved even if there is a subtle difference in a conformational structure, a given molecule can be processed in a unified manner, and large-scale computer processing can be performed.

Further, according to the invention, by including a rule in accordance with the IUPAC Notation, narrower classification can be achieved and a more precise conformation analysis can be performed.

Further, although it was impossible to compare conformations of active species of Taxol based on the conventionally used notations themselves such as T-Taxol and PTX-NY, according to the invention, it is possible to easily compare a difference in the conformations of the respective active species by the notation method to be used in this analysis technique. Further, it becomes easy to create a database of a molecule on a block basis. Moreover, by using the method in combination with vibrational circular dichroism data, a conformational structure having a large abundance ratio in a liquid phase state can be extracted.

Accordingly, the invention can be utilized in, for example, novel drug designing which has been performed with reference to conformations of active species of Taxol and the like, and exploitation of application thereof such as evaluation of an effect of a hazardous substance on the human body utilizing a structure-activity relationship or the like, or drug discovery using a pharmacological proteomic approach is sufficiently expected.

Further, in order to achieve the above object, the present invention seventhly provides preferably a conformational notation method which is a method for performing a simple conformational notation with which, even if there is a subtle difference in a conformational structure, comparison of the conformational structure can be easily performed using a simplified symbol, a given molecule can be processed in a unified manner, and large-scale computer processing can be performed. The conformational notation method is characterized in that: a processing section receives an input of a molecular model of a compound to be analyzed; with respect to a structure capable of uniquely determining a conformation with one conformational notation (hereinafter, referred to as an encoded conformational notation) expressed in a notation using two types of codes determined by dividing 360 degrees into six segments, putting predetermined codes to the respective divided segments, further dividing the respective divided segments into two segments and putting other predetermined codes to the respective further divided segments by expressing each chemical binding site in the encoded conformational notation based on the received molecular model, the processing section extracts an encoded conformational notation which is required for the conformational notation and is obtained by leaving a notation of a chemical bond of interest and omitting an unnecessary notation from the molecular model and stores the extracted encoded conformational notation in a storage section; the processing section stores physical property values including an observed measured value and a calculated predicted value which are in a correspondence relation with the compound to be analyzed in the storage section; and the processing section extracts the encoded conformational notation and the physical property values which are in a correspondence relation with the compound to be analyzed from the storage section.

Further, the invention eighthly provides a conformational notation method characterized in that in the above method, in the case where a plurality of molecular models correspond to one encoded conformational notation, the conformation can be uniquely determined by putting a new code.

Further, the invention ninthly provides a conformational notation method characterized in that in the above seventh method, in the case where one molecular model can be expressed in a plurality of the encoded conformational notations, the conformation can be uniquely determined by following a predetermined priority rule and selecting the encoded conformational notation.

Further, the invention tenthly provides a conformational notation method characterized in that in the above seventh method, the above eighth method and the above tenth method are combined.

Further, the invention eleventhly provides preferably a conformational notation device which is a device for performing a simple conformational notation with which, even if there is a subtle difference in a conformational structure, comparison of the conformational structure can be easily performed using a simplified symbol, a given molecule can be processed in a unified manner, and large-scale computer processing can be performed. The conformational notation device is characterized in that: a processing section receives an input of a molecular model of a compound to be analyzed; with respect to a structure capable of uniquely determining a conformation with one conformational notation (hereinafter, referred to as an encoded conformational notation) expressed in a notation using two types of codes determined by dividing 360 degrees into six segments, putting predetermined codes to the respective divided segments, further dividing the respective divided segments into two segments and putting other predetermined codes to the respective further divided segments by expressing each chemical binding site in the encoded conformational notation based on the received molecular model, the processing section extracts an encoded conformational notation which is required for the conformational notation and is obtained by leaving a notation of a chemical bond of interest and omitting an unnecessary notation from the molecular model and stores the extracted encoded conformational notation in a storage section; the processing section stores physical property values including an observed measured value and a calculated predicted value which are in a correspondence relation with the compound to be analyzed in the storage section; and the processing section extracts the encoded conformational notation and the physical property values which are in a correspondence relation with the compound to be analyzed from the storage section.

Further, the invention twelfthly provides a conformational notation device characterized in that in the above device, in the case where a plurality of molecular models correspond to one encoded conformational notation, the conformation can be uniquely determined by putting a new code.

Further, the invention thirteenthly provides a conformational notation device characterized in that in the above eleventh device, in the case where one molecular model can be expressed in a plurality of the encoded conformational notations, the conformation can be uniquely determined by following a predetermined priority rule and selecting the encoded conformational notation.

Further, the invention fourteenthly provides a conformational notation device characterized in that in the above eleventh device, the above twelfth device and the above thirteenth device are combined.

According to the present invention, even if there is a subtle difference in a conformational structure, comparison of the conformational structure can be easily performed using a simplified symbol, a given molecule can be processed in a unified manner, and large-scale computer processing can be performed.

That is, according to the invention, encoding of a dihedral angle and the like are more precisely defined than the rule in accordance with the IUPAC Nomenclature, and therefore, even in the case (3) where a ligand which provides the smallest torsion angle is selected when all ligands are the same as a priority rule for ligands of the IUPAC Nomenclature, a conformation can be uniquely determined, a given molecule can be processed in a unified manner, and large-scale computer processing can be performed.

Further, although it was impossible to uniquely determine a conformation with a conventionally used notation itself for levofloxacin, ibuprofen or the like, according to the invention, it is possible to easily compare a difference in the respective conformations by the notation method to be used in this analysis technique. Further, it becomes easy to create a database of a molecule on a fragment basis. Moreover, by using the method in combination with vibrational circular dichroism data, a notation of a conformation having a large abundance ratio in a liquid phase state can be extracted.

Accordingly, the invention can be utilized in, for example, novel drug designing which has been performed with reference to conformations of active species of levofloxacin, and exploitation of application thereof such as evaluation of an effect of a hazardous substance on the human body utilizing a structure-activity relationship or the like, or drug discovery using a pharmacological proteomic approach is sufficiently expected.

DETAILED DESCRIPTION OF THE INVENTION

Hereinafter, the present invention will be described in detail with reference to preferred embodiments.

1. First Embodiment

Figure 1:
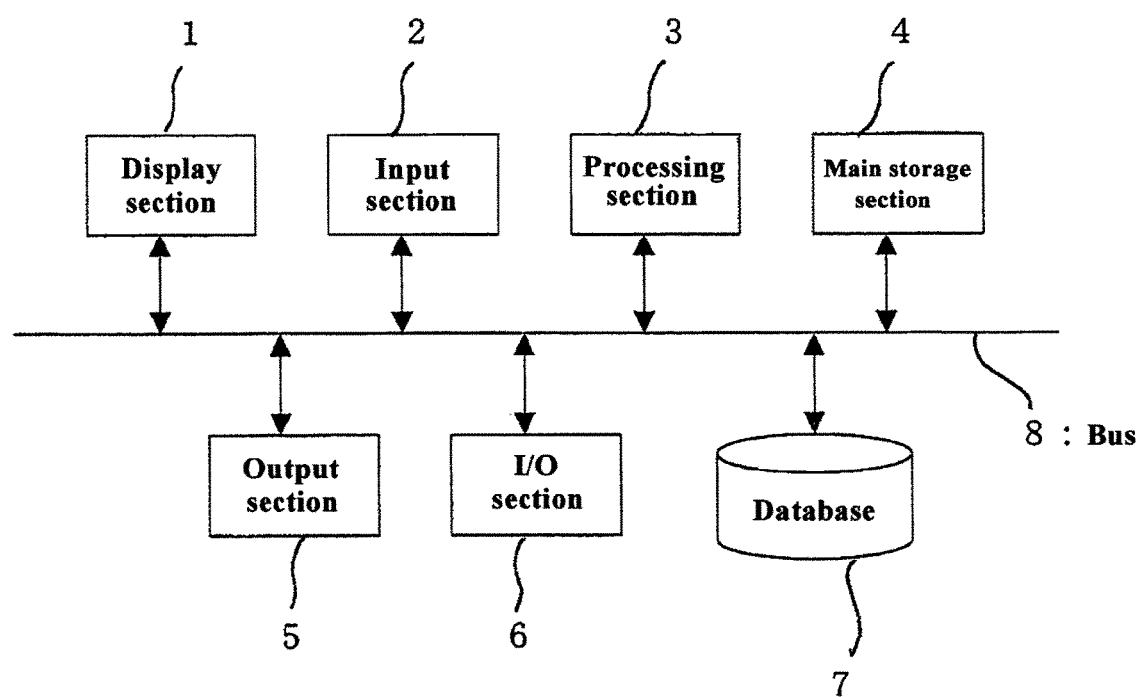
FIG. 1 It is a system block diagram of a conformation analysis device of the invention and a conformational notation device of the invention.

FIG. 1 is a system block diagram of a conformation analysis device of the invention. This conformation analysis device comprises a display section 1, an input section 2, a processing section 3, a main storage section 4, an output section 5, an external interface (I/O) section 6 and a database 7 and the respective sections are connected to one another through a bus 8. Such a conformation analysis device can be constructed by, for example, a personal computer on which a program for performing a conformation analysis has been installed or the like.

The display section 1 is composed of a CRT, a liquid crystal display or the like and performs screen display for a conformation analysis. The input section 2 is composed of any of various input units such as a keyboard and is used for inputting data or information required by a user. The processing section 3 can be constituted by a CPU and carries out various controls, operations or the like for a conformation analysis. The main storage section 4 stores a program or the like for a conformation analysis. The output section 5 is composed of a printer or the like and outputs a processing result or the like to a user. The external interface (I/O) section 6 provides connection to other terminal equipment or the like via the LAN, internet or the like. The database 7 rewritably stores various data or the like for a conformation analysis.

In the conformation analysis device of the invention, an encoded notation method including a rule in accordance with the IUPAC Notation is used. Therefore, it does not matter if the compound to be analyzed of the invention has a chain structure or a cyclic structure in a part of its structure as long as it is an organic compound. Further, it does not matter if the compound to be analyzed is substituted with a functional group such as an ester group, a carbonyl group, a hydroxyl group, a phenyl group, alkene, halogen, a phosphorus atom or a sulfur atom. Further, it does not matter if the compound to be analyzed has a structure bound through a bond other than a covalent bond such as a hydrogen bond or a coordinate bond. However, in the case where a conformational structure having a large abundance ratio in a liquid phase is extracted in combination with vibrational circular dichroism data, the compound to be analyzed is limited to an optically active molecule.

As such an organic compound, for example, compounds as shown below can be exemplified:

thalidomide, thalidomide dimer, 5'-hydroxythalidomide, phthalimide, dioxopiperidine, paclitaxel, paclitaxel tail, paclitaxel tail methyl ester, baccatin III, benzamide, malathion, diethyl succinate, 2-mercapto diethyl succinate, 2-butanol, 2-pentanol, 2-hexanol, 2-heptanol, 2-octanol, 2-nonanol, 2-decanol, 2-methyl-1-butanol, 3-methyl-1-pentanol, 4-methyl-1-hexanol, 5-methyl-1-heptanol, 6-methyl-1-octanol, cis-permethrin, cis-3-(2,2-dichlorovinyl)-2,2-dimethylcyclopropan carboxylic acid benzyl ester, cis-3-(2,2-dichlorovinyl)-2,2-dimethylcyclopropan carboxylic acid methyl ester, 3-phenoxybenzyl alcohol, cholesterol acetate, cholesterol propionate, n-butyric acid cholesterol ester, cholesterol n-valerate, cholesterol n-hexanoate, cholesterol n-heptanoate, cholesterol n-caprylate, cholesterol pelargonate, cholesterol n-caprate, cholesterol laurate, cholesterol myristate, cholesterol palmitate, cholesterol, β-cholestanol, cholesteryl chloride, cholesteryl bromide, cholesterol methyl carbonate, cholesterol ethyl carbonate, cholesterol n-butyl carbonate, cholesterol n-amyl carbonate, cholesterol n-hexyl carbonate, cholesterol n-heptyl carbonate, cholesterol n-nonyl carbonate and cholesterol oleyl carbonate.

An outline of the conformation analysis using the conformation analysis device of this embodiment will be described. First, the processing section 3 receives an input of a chemical structural formula of a compound to be analyzed. Subsequently, the processing section 3 puts a predetermined code indicating a dihedral angle to each chemical binding site based on the received chemical structural formula, extracts an encoded conformational notation of interest with respect to a structure capable of uniquely determining a conformation with one conformational notation and stores the extracted encoded conformational notation in the database 7. Subsequently, the processing section 3 creates a molecular model based on the extracted encoded conformational notation, performs geometry optimization and frequency calculation for the created molecular model and determines a geometry optimized structure and a physical property value of the geometry optimized structure. Then, the processing section 3 extracts the encoded conformational notation from the database 7 and performs a homology analysis based on the notation.

Figure 2:
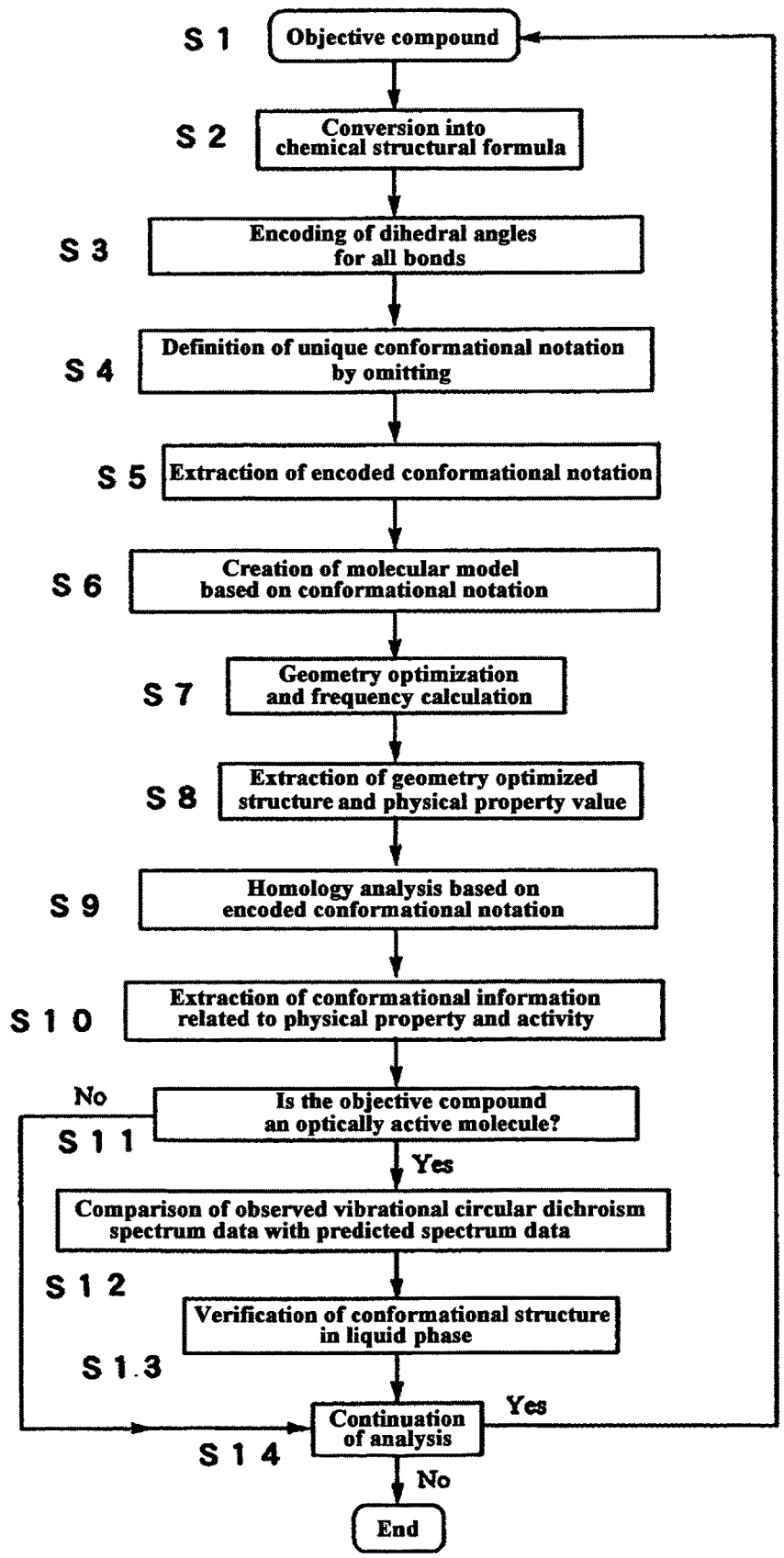
FIG. 2 It is a flowchart of analysis processing according to the invention.

A more detailed description will be made using the flowchart of FIG. 2. In the invention, first, by putting a code indicating a dihedral angle to each chemical binding site based on the chemical structural formula, a definition of a conformational notation is made (Steps S1 to S3). In this case, for example, compound names may be linked to chemical structural formulae, respectively, and the information thereof is stored in the database 7 in advance in such a manner that when a compound name is inputted in the input section 2 by a user, it can be converted into a corresponding chemical structural formula.

Subsequently, a definition of a notation uniquely indicating a conformation is made by leaving a notation of a chemical bond of interest and omitting an unnecessary notation with respect to a structure capable of uniquely determining a conformation with one conformational notation such as a case of having a cyclic structure (Steps S4 and S5). Based on this definition, the notation expressed in only extracted codes is used for a conformation analysis. If it is simpler to notate a compound in a separated manner on a block basis from the viewpoint of creation of a database, a notation comprising a combination of a block and a code can be employed.

Figure 3:
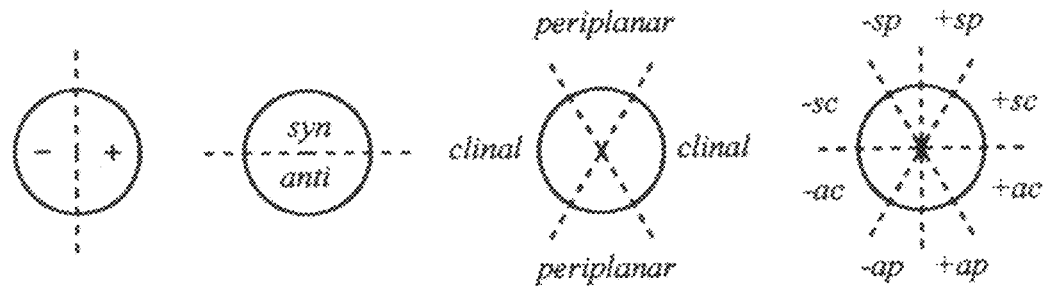
FIG. 3 It is a view showing classification of conformation into 8 classes based on the IUPAC Notation.

As the method for putting a code indicating a dihedral angle, a rule in accordance with the IUPAC Notation is included from the viewpoint of standardization. That is, in the IUPAC Notation, it is determined that a conformation is notated based on a dihedral angle formed by ligands bound to the respective ends of chemical bonds of interest. Further, as a priority rule for ligands, the followings are determined: (1) when the ligands are all different, the most superior ligand based on a priority rule determined by the R/S notation, (2) when one ligand is different from the others, the ligand itself regardless of the priority, and (3) when all ligands are the same, a ligand which provides the smallest torsion angle. Further, it is determined that classification is made into 8 classes using the expressions of +/−, syn/anti, and periplanar/clinal. A chart of classification into these 8 classes is shown in FIG. 3. In the invention, a conformation analysis is performed by including these rules.

Figure 4:
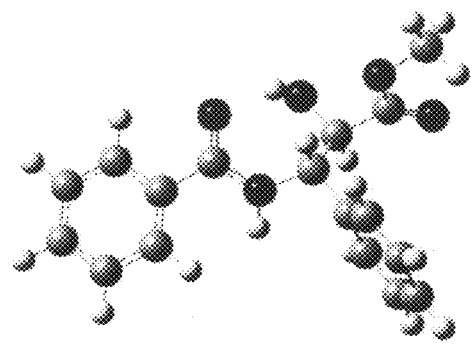
FIG. 4 It is a view showing a molecular model of a conformation represented by tail+4322324.

Further, in the invention, for example, 4 classes, ap, +sc, −sc, and sp are mainly used, and in the case where a detail description is needed, by adding +ac, −ac, +ap, −ap, +sp, and −sp thereto, a total of 10 classes are used. Specifically, by putting codes as follows: ap=1, +sc=2, −sc=3, sp=4, +ac=5, −ac=6, +ap=7, −ap=8, +sp=+, and −sp=−, a conformation is notated. For example, in the case of paclitaxel tail methyl ester, it is represented by the chemical structural formula of (PhCONH)PhCHOHCHCO(OMe), and when the conformation thereof is (Ph+CO4NH)3Ph2CH$_2$OH3CH2CO4(OMe), the conformation is notated by tail+4322324. A molecular model of a conformation represented by tail+4322324 is shown in FIG. 4. Here, Ph denotes a phenyl group, and Me denotes a methyl group (hereinafter the same shall apply).

Figure 5:
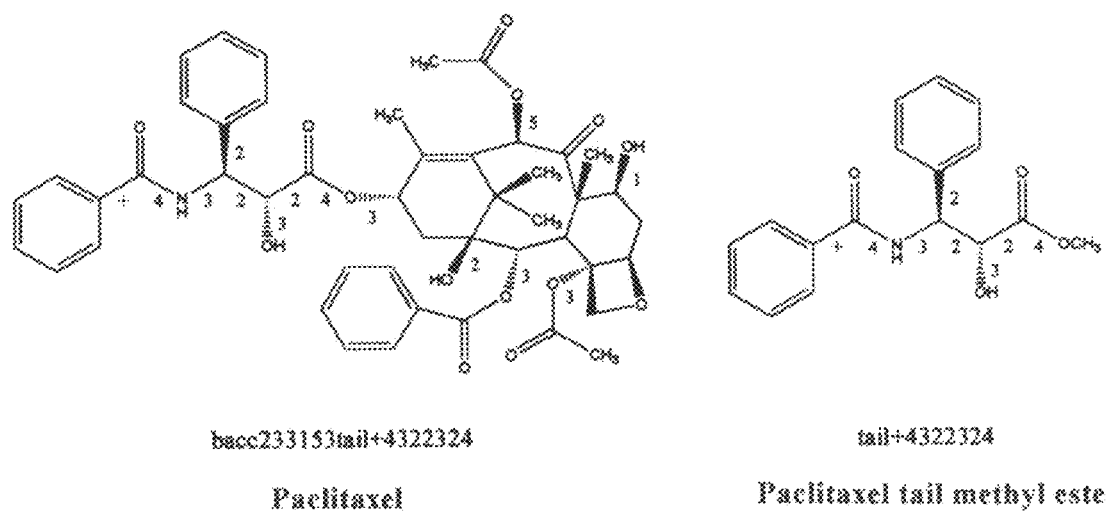
FIG. 5 It is a view showing chemical structural formulae of paclitaxel and paclitaxel tail methyl ester.

Further, in the case of paclitaxel, a conformation defined as baccOH2(PhCOO)3(MeCOO)3OH1(MeCOO)5(tail+ 4322324)3 may be notated by bacc233153(tail+4322324). The chemical structural formulae of paclitaxel and paclitaxel tail methyl ester are shown in FIG. 5.

In the conformation analysis device of this embodiment, an analysis is performed by linking to the above-mentioned conformational notation. That is, a molecular model is created based on the conformational notation (Step S6), geometry optimization and frequency calculation for the created molecular model are performed (Step S7), and an energy value and a physical property value of the resulting geometry optimized structure are determined (Step S8). Further, a homology analysis is performed using the conformational notation (Step S9), and conformational information related to a physical property and an activity is analyzed (Step S10). Here, a method for geometry optimization and frequency calculation for the created molecular model is not particularly limited, however, preferably a molecular orbital calculation method based on a density functional method using the B3LYP functional is employed.

Further, in the invention, in the case where the compound to be analyzed is an optically active molecule, by confirming that an observed vibrational circular dichroism spectrum coincides with a predicted spectrum obtained from candidate conformations, a conformational structure of an optically active molecule in a liquid phase can be verified (Steps S11 to S13).

In order to search for conformation candidates, for example, a method described in the above Patent document 2 (JP-A-2005-91164) may be used. The method for obtaining a predicted spectrum from candidate conformations is not particularly limited, however, the following method is preferably used. A Gibbs free energy is obtained from frequency calculation by a density functional method using the B3LYP functional, which is converted into a Boltzmann population. Then, a value obtained by multiplying a predicted spectrum of each conformation by a Boltzmann population factor is added thereto, whereby an average spectrum is obtained.

Incidentally, the order of the process of encoding of a conformational notation and the process of geometry optimization for a molecular model and extraction of a physical property value may be changed. Further, for example, with respect to a conformational structure obtained from a different measurement analysis as a conformational structure of an organic molecule incorporated in a protein, a homology analysis may be performed using the conformational notation.

The device to be used for the measurement of infrared and vibrational circular dichroism spectra to be used in the invention is not particularly limited, and as the infrared spectrometer and the vibrational circular dichroism spectrometer, for example, Chiralir manufactured by Bomem/ BioTools can be used.

As a solvent to be used for the measurement of vibrational circular dichroism, either of a hydrophobic solvent and a hydrophilic solvent can be used, however, preferably carbon tetrachloride, deuterated chloroform, deuterated methylene chloride, deuterated dimethyl sulfoxide, water or the like is used. In the case where the objective compound is liquid, it can be measured as a neat liquid.

As a window plate of a sample cell, any window plate can be used as long as it is made of a material transmitting infrared radiation, however, a NaCl plate or a BaF$_2$ plate is preferred.

An accumulation time for measurement of vibrational circular dichroism is not particularly limited, however, in order to obtain sufficient S/N, it is preferably from 20 minutes to 4 hours.

An approximation method to be used for fitting of the vibrational circular dichroism band is not particularly limited, however, the Lorentz function approximation or the Gauss function approximation is preferably used.

2. Second Embodiment

A system block diagram of a conformational notation device of the invention of the Second Embodiment is basically the same with that of a conformation analysis device of the above First Embodiment, thus the system block diagram will be explained with reference to FIG. 1.

This conformational notation device comprises a display section 1, an input section 2, a processing section 3, a main storage section 4, an output section 5, an external interface (I/O) section 6 and a database 7 and the respective sections are connected to one another through a bus 8. Such a conformational notation device can be constructed by, for example, a personal computer on which a program for performing a conformational notation has been installed or the like.

The display section 1 is composed of a CRT, a liquid crystal display or the like and performs screen display for a conformational notation. The input section 2 is composed of any of various input units such as a keyboard and is used for inputting data or information required by a user. The processing section 3 can be constituted by a CPU and carries out various controls, operations or the like for a conformational notation. The main storage section 4 stores a program or the like for a conformational notation. The output section 5 is composed of a printer or the like and outputs a processing result or the like to a user. The external interface (I/O) section 6 provides connection to other terminal equipment or the like via the LAN, internet or the like. The database 7 rewritably stores various data or the like for a conformational notation.

In the conformational notation device of the invention, a notation method in which encoding of a dihedral angle is more precisely defined than the rule in accordance with the IUPAC Nomenclature is used. Therefore, it does not matter if the compound to be analyzed of the invention has a chain structure or a cyclic structure in a part of its structure as long as it is an organic compound. Further, it does not matter if the compound to be analyzed is substituted with a functional group such as an ester group, a carbonyl group, a hydroxyl group, a phenyl group, alkene, halogen, a phosphorus atom or a sulfur atom. Further, it does not matter if the compound to be analyzed has a structure bound through a bond other than a covalent bond such as a hydrogen bond or a coordinate bond. However, in the case where a conformational structure having a large abundance ratio in a liquid phase is extracted in combination with vibrational circular dichroism data, the compound to be analyzed is limited to an optically active molecule.

As such an organic compound, for example, compounds as shown below can be exemplified:

levofloxacin, piperazine, ibuprofen, ibuprofen dimer, 2-phenyl propionate, thalidomide, thalidomide dimer, 5'-hydroxythalidomide, phthalimide, dioxopiperidine, paclitaxel, paclitaxel tail, paclitaxel tail methyl ester, baccatin III, benzamide, malathion, diethyl succinate, 2-mercapto diethyl succinate, 2-butanol, 2-pentanol, 2-hexanol, 2-heptanol, 2-octanol, 2-nonanol, 2-decanol, 2-methyl-1-butanol, 3-methyl-1-pentanol, 4-methyl-1-hexanol, 5-methyl-1-heptanol, 6-methyl-1-octanol, cis-permethrin, cis-3-(2,2-dichlorovinyl)-2,2-dimethylcyclopropan carboxylic acid benzyl ester, cis-3-(2,2-dichlorovinyl)-2,2-dimethylcyclopropan carboxylic acid methyl ester, 3-phenoxybenzyl alcohol, cholesterol acetate, cholesterol propionate, n-butyric acid cholesterol ester, cholesterol n-valerate, cholesterol n-hexanoate, cholesterol n-heptanoate, cholesterol n-caprylate, cholesterol pelargonate, cholesterol n-caprate, cholesterol laurate, cholesterol myristate, cholesterol palmitate, cholesterol, β-cholestanol, cholesteryl chloride, cholesteryl bromide, cholesterol methyl carbonate, cholesterol ethyl carbonate, cholesterol n-butyl carbonate, cholesterol n-amyl carbonate, cholesterol n-hexyl carbonate, cholesterol n-heptyl carbonate, cholesterol n-nonyl carbonate and cholesterol oleyl carbonate.

An outline of the conformational notation using the conformational notation device of this embodiment will be described. First, the processing section 3 receives an input of a molecular model of a compound to be analyzed. Subsequently, the processing section 3 puts a code predetermined based on a dihedral angle to each chemical binding site according to the received molecular model, extracts an encoded conformational notation of interest with respect to a structure capable of uniquely determining a conformation with one conformational notation and stores the extracted encoded conformational notation in the database 7. Subsequently, the processing section 3 performs geometry optimization and frequency calculation for the molecular model based on the extracted encoded conformational notation and determines a geometry optimized structure and a physical property value of the geometry optimized structure. Then, in the case where a structural change occurs as a result of geometry optimization, the processing section 3 extracts the encoded conformational notation of the structure and stores the extracted encoded conformational notation in the database 7. The processing section 3 extracts the encoded conformational notation and physical property value corresponding to the molecular model of interest from the database 7 and makes a notation. If necessary, the processing section 3 receives an input of an observed physical property value or molecular structure of the compound to be analyzed. Subsequently, the processing section 3 stores the observed physical property value in the database 7. Alternatively, the processing section 3 puts a code predetermined based on a dihedral angle to each chemical binding site according to the received observed molecular structure and extracts an encoded conformational notation of interest with respect to a structure capable of uniquely determining a conformation with one conformational notation and stores the extracted encoded conformational notation in the database 7. The processing section 3 extracts required data among the physical property value of the geometry optimized structure, the geometry optimized molecular model, the observed physical property value and the observed molecular structure along with the encoded conformational notation thereof, and performs a homology analysis based on the extracted encoded conformational notation. Further, the processing section 3 performs numerical calculation such as averaging processing using an abundance ratio as needed and performs a homology analysis based on the encoded conformational notation using the obtained result. The processing section 3 notates the result of the homology analysis along with the encoded conformational notation.

Figure 13:
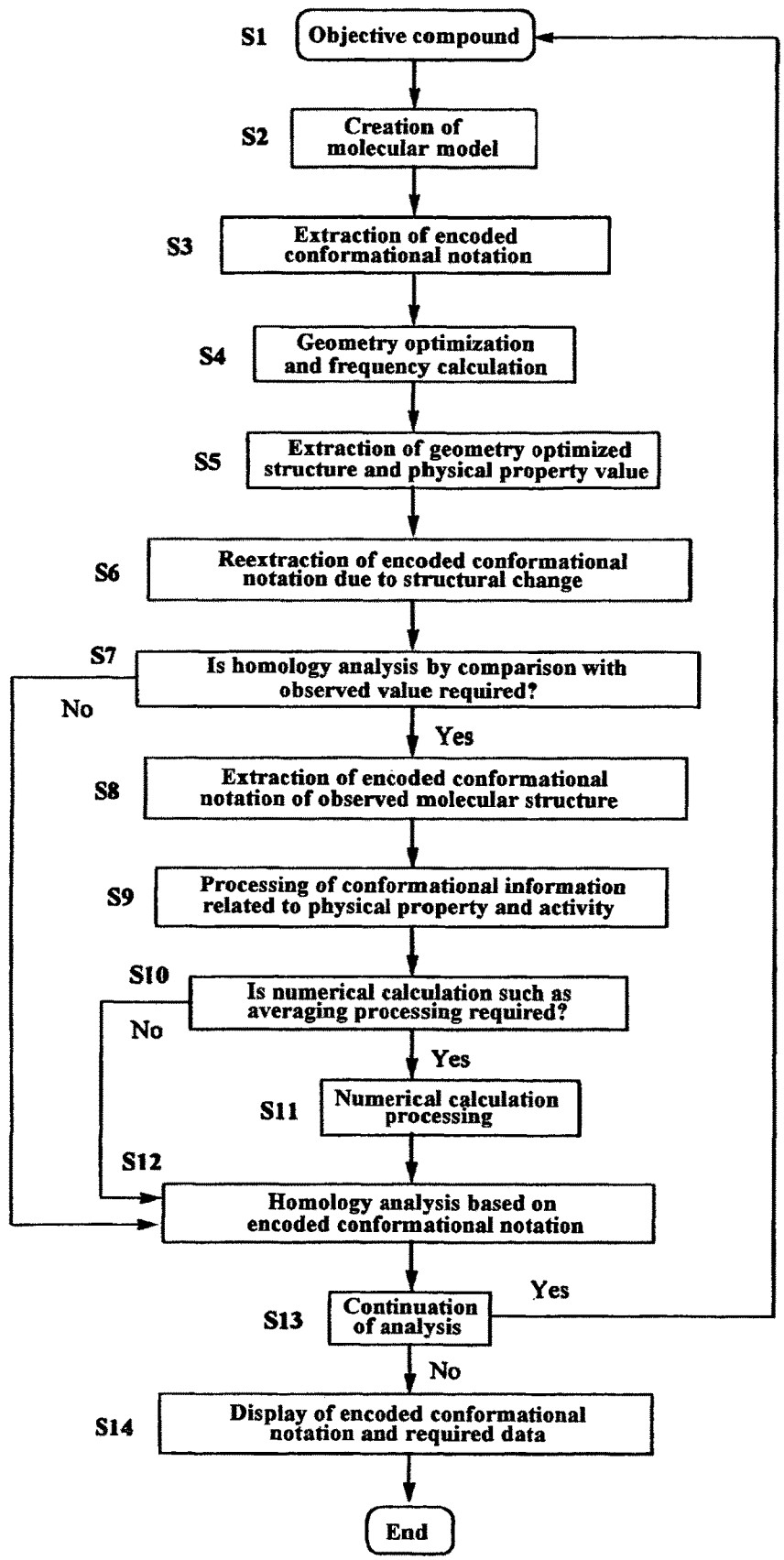
FIG. 13 It is a flowchart of analysis processing according to the invention.

A more detailed description will be made using the flowchart of FIG. 13. In the invention, first, by putting a code predetermined based on a dihedral angle to each chemical binding site according to the molecular model, a definition of a conformational notation which uniquely determines a conformation is made (Steps S1 to S3). In this case, for example, compound names, chemical structural formulae and molecular models may be linked to one another, respectively, and the information thereof is stored in the database 7 in advance in such a manner that when a compound name or a chemical structural formula is inputted in the input section 2 by a user, it can be converted into a corresponding molecular model.

To be more specific, with respect to a structure capable of uniquely determining a conformation with one conformational notation such as a case of having a cyclic structure, a definition of a notation uniquely indicating a conformation is made by leaving a notation of a chemical bond of interest and omitting an unnecessary notation (Step S3). Based on this definition, the notation expressed in only extracted codes is used for a conformation analysis. If it is simpler to notate a compound in a separated manner on a fragment basis from the viewpoint of creation of a database, a notation comprising a combination of a prefix of a fragment and a code may be used. Further, in case a position of a hydrogen atom cannot be determined as in the case of X-ray crystal structural analysis data and the like, a code indicating only a position of a corresponding dihedral angle in place of a code predetermined based on a dihedral angle may be used.

Figure 14:
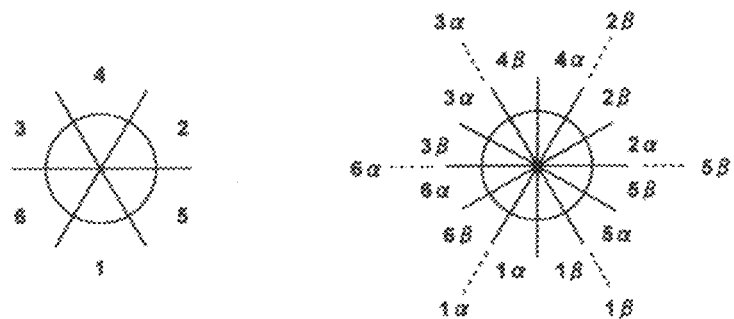
FIG. 14 It is a view showing classification of codes indicating dihedral angles to be used for an encoded conformational notation.

Here, the method for putting a code indicating a dihedral angle is generally as follows. 360 degrees are divided into six segments, and predetermined codes such as 1 to 6 shown in FIG. 14 are put to the respective divided segments, and a conformation is notated mainly using such codes. It rarely happens that conformations which should be determined to be two different conformations are notated by the same code by this classification. Therefore, in this case, each of the divided six segments is further divided into two segments, and predetermined codes such as a (clockwise) and β (counterclockwise) are put to the respective divided two segments, and a conformation is notated using codes corresponding to the divided 12 segments shown in FIG. 14 expressed in a combination of mainly these two types of codes. Further, in case a corresponding dihedral angle happens to be located on a boundary line, a code shown in FIG. 14 can be used on the boundary line.

Figure 15:
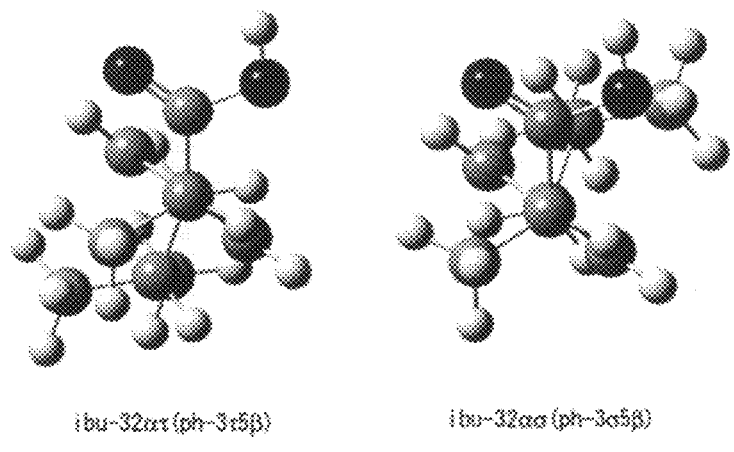
FIG. 15 It is an illustrative view showing that a conformation is made to be uniquely notatable by using codes such as ρ (cis) and τ (trans) based on a relative positional relation in the case where a plurality of molecular models correspond to one encoded conformational notation.

Further, in the invention, in the rule in accordance with the IUPAC Nomenclature, in the case (3) where a ligand which provides the smallest torsion angle is selected when all ligands are the same, there may be a case where a plurality of molecular models correspond to one encoded conformational notation. In this case, a conformation is made to be uniquely notatable by using new codes such as ρ (cis) and τ (trans) based on a relative positional relation. For example, in the case where a dihedral angle is determined in an aromatic ring bound to a propionate moiety in (S)-ibuprofen, which corresponds to the case (3) where a ligand which provides the smallest torsion angle is selected when all ligands are the same, there are two types of conformational structures represented by the same notation shown in FIG. 15 in the expression of an encoded conformational notation of ibu-32α(ph-35β). In this case, by employing a relative positional relation between bonds of interest, discrimination is made using codes of ρ (cis) and τ (trans).

Figure 16:
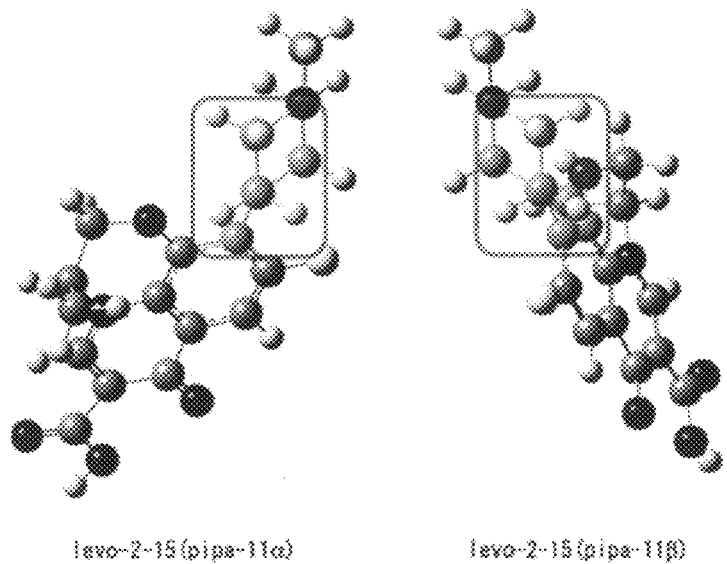
FIG. 16 It is an illustrative view for showing a priority rule in the case where one molecular model can be expressed in a plurality of encoded conformational notations.

Further, in the rule in accordance with the IUPAC Nomenclature, in the case (3) where a ligand which provides the smallest torsion angle is selected when all ligands are the same, there may be a case where dihedral angles for the ligand which cannot be discriminated in a clockwise or counterclockwise rotation are the same. In this case, one molecular model can be expressed in a plurality of encoded conformational notations, and therefore, priority is given to a ligand which provides the smallest torsion angle in a clockwise rotation. For example, in levofloxacin, as for the dihedral angles for the piperazine ring shown in FIG. 16, the dihedral angles for the ligand have the same absolute value but opposite signs because the piperazine ring itself is symmetric and can be expressed in two types of encoded conformational notations. By adopting the priority rule, a notation of the conformation is uniquely defined to be levo-2-15(pipa-11β). With respect to other rules, the rules in accordance with the IUPAC Nomenclature described in the above-mentioned Patent document 3 (PCT/JP 2008/051673) or Non-patent document 4 (H. Izumi et al., J. Org. Chem., 2008, 73, 2367) are followed.

In the conformational notation device of this embodiment, an analysis is performed by linking to the above-mentioned conformational notation and thereafter, an encoded conformational notation is displayed along with the information such as a necessary physical property value. That is, geometry optimization and frequency calculation for a molecular model corresponding to the conformational notation are performed (Step S4), and an energy value and a physical property value of the resulting geometry optimized structure are determined (Step S5). Further, whether or not a structural change occurs before and after the geometry optimization is examined, and if a structural change occurs, by putting a code predetermined based on a dihedral angle to each chemical binding site according to the molecular model once again, an encoded conformational notation is extracted based on a definition of a conformational notation uniquely determining a conformation (Step S6). Here, in the case where homology comparison is performed with only an observed physical property value, the steps of the geometry optimization and frequency calculation may be omitted. Subsequently, in the case where it is not necessary to perform comparison with an observed physical property value, homology comparison of a physical property value of the geometry optimized structure is performed using the conformational notation (Step S12). Here, a method for geometry optimization and frequency calculation for a molecular model is not particularly limited, however, preferably a molecular orbital calculation by a density functional method using the B3LYP functional is employed.

In the case where comparison with an observed physical property value is performed, first, by putting a code predetermined based on a dihedral angle to each chemical binding site with respect to an observed molecular structure to be compared such as X-ray crystal structural analysis data, an encoded conformational notation is extracted based on a definition of a conformational notation uniquely determining a conformation (Step S8). In the case where an observed physical property value is not accompanied by observed molecular structure data as the case of comparing vibrational circular dichroism data, Step S8 can be omitted. Subsequently, processing of conformational information is performed so as to perform a homology analysis of Step S12 with respect to observed physical property value and activity (Step S9). Further, in the invention, in the case where a plurality of conformational structures have to be considered as the case of performing comparison with a vibrational circular dichroism spectrum in a liquid phase, numerical calculation processing such as averaging processing of physical property values or creation of a database of the encoded conformational notations of a plurality of conformational structures used can be performed (Steps S10 to S12). When comparison with a vibrational circular dichroism spectrum in a liquid phase is performed, for example, the method described in the above-mentioned Patent document 3 (PCT/JP 2008/051673) may be used.

Incidentally, the order of the process of encoding of a conformational notation, the process of geometry optimization for a molecular model and extraction of a physical property value and the process of a homology analysis may be changed. Further, for example, with respect to a conformational structure obtained from a different measurement analysis as a conformational structure of an organic molecule incorporated in a protein, a homology analysis may be performed using the conformational notation according to the method described in the above-mentioned Patent document 3 (PCT/JP 2008/051673).

EXAMPLES

Hereinafter, the present invention will be described in further detail with reference to Examples, but it should be understood that the invention is not limited to those examples.

Example 1

Figure 6:
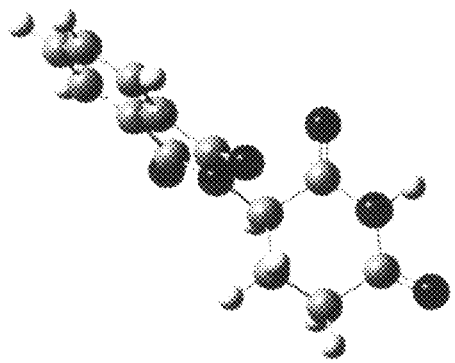
FIG. 6 It is a view showing a molecular model of a conformation represented by pipe4(phim3).

A definition of a conformational notation was made by putting a code indicating a dihedral angle to each chemical binding site of thalidomide represented by the following chemical structural formula (I). Subsequently, a definition of a notation uniquely indicating a conformation was made by leaving a notation of a chemical bond of interest and omitting an unnecessary notation. Based on this definition, a notation expressed in only extracted codes was determined. Subsequently, with respect to a molecular model based on the encoded conformational notation, geometry optimization and frequency calculation by a density functional method using the B3LYP functional were performed and an energy value of the resulting geometry optimized structure was obtained. A homology analysis was performed using the encoded conformational notation, and pipe4 (phim3) which is a conformational structure having a large abundance ratio in a liquid phase was extracted. The encoded conformational notations and the results of the homology analysis are shown in Table 1. A molecular model of a conformation represented by pipe4(phim3) is shown in FIG. 6.

TABLE 1

(I)

pipe4(phim3)

Encoded conformational notations and analysis results for thalidomide (I)

| Conformation | ΔG (kcal mol$^{-1}$) | Abundance ratio |
| --- | --- | --- |
| pipe4(phim3) | 0 | 0.974685927 |
| pipe3(phim3) | 2.163072213 | 0.025314073 |

Example 2

Figure 7:
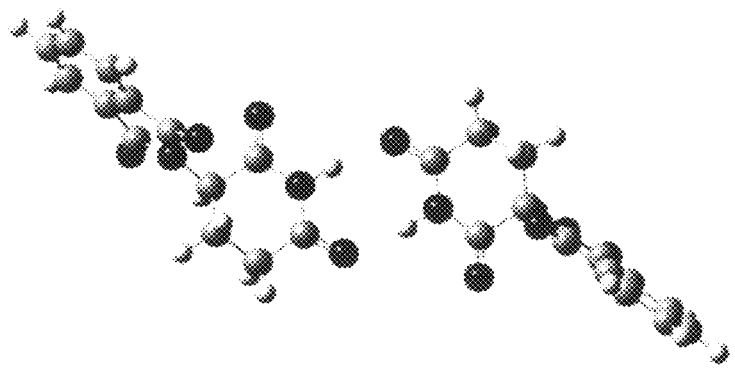
FIG. 7 It is a view showing a molecular model of a conformation represented by pipe4(phim3)pipe4(phim3)BB.

A definition of a conformational notation was made by putting a code indicating a dihedral angle to each chemical binding site of a series of thalidomide dimers represented by the following chemical structural formulae (II). Subsequently, a definition of a notation uniquely indicating a conformation was made by leaving a notation of a chemical bond of interest and omitting an unnecessary notation. Based on this definition, a notation expressed in only extracted codes was determined. Subsequently, with respect to a molecular model based on the encoded conformational notation, geometry optimization and frequency calculation by a density functional method using the B3LYP functional were performed and an energy value of the resulting geometry optimized structure was obtained. A homology analysis was performed using the encoded conformational notation, and pipe4(phim3)pipe4(phim3)BB which is a conformational structure having a large abundance ratio in a liquid phase was extracted. The encoded conformational notations and the results of the homology analysis are shown in Table 2. A molecular model of a conformation represented by pipe4(phim3)pipe4(phim3)BB is shown in FIG. 7.

TABLE 2

(II)

pipe4(phim3)pipe4(phim3)AA pipe4(phim3)pipe4(phim3)AB pipe4(phim3)pipe4(phim3)BB Encoded conformational notations and analysis results for thalidomide dimer (II)

| Conformation | ΔG (kcal mol$^{-1}$) | Abundance ratio |
| --- | --- | --- |
| pipe4(phim3)pipe4(phim3)AA | 0.353977199 | 0.235970024 |
| pipe4(phim3)pipe4(phim3)AB | 0.146052513 | 0.335168207 |
| pipe4(phim3)pipe4(phim3)BB | 0 | 0.428861769 |

Example 3

Figure 8:
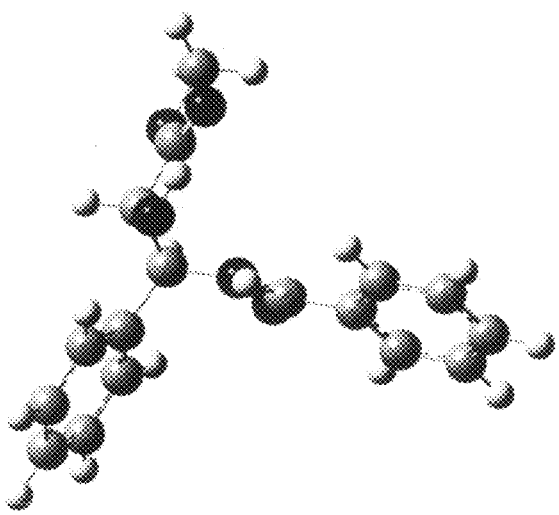
FIG. 8 It is a view showing a molecular model of a conformation represented by tail-4633+14.

A definition of a conformational notation was made by putting a code indicating a dihedral angle to each chemical binding site of paclitaxel tail methyl ester represented by the following chemical structural formula (III). Subsequently, a definition of a notation uniquely indicating a conformation was made by leaving a notation of a chemical bond of interest and omitting an unnecessary notation. Based on this definition, a notation expressed in only extracted codes was determined. Subsequently, with respect to a molecular model based on the encoded conformational notation, geometry optimization and frequency calculation by a density functional method using the B3LYP functional were performed and an energy value of the resulting geometry optimized structure was obtained. A homology analysis was performed using the encoded conformational notation, and tail-4633+14 which is a conformational structure having a large abundance ratio was extracted. The encoded conformational notations and the results of the homology analysis are shown in Table 3. A molecular model of a conformation represented by tail-4633+14 is shown in FIG. 8.

TABLE 3

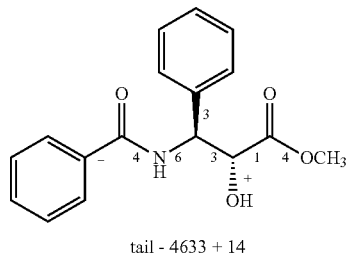

(III)

tail − 4633 + 14

Encoded conformational notations and analysis results for paclitaxel tail methyl ester

| Conformation | ΔG (kcal mol$^{-1}$) | Abundance ratio |
|---|---|---|
| tail − 4633 + 14 | 0 | 0.265490697 |
| tail + 4633 + 14 | 0.004744603 | 0.263373199 |
| tail + 4333 − 14 | 0.012902986 | 0.259771555 |
| tail − 4333 − 14 | 0.309198148 | 0.157547404 |
| tail − 46 + 13 + 4 | 1.67846356 | 0.015622777 |
| tail − 46 + 1414 | 1.920590615 | 0.010382032 |
| tail + 46 + 13 + 4 | 2.03012669 | 0.008629665 |
| tail + 46 + 1414 | 2.205840534 | 0.00641502 |
| tail + 4322334 | 2.641861967 | 0.003073267 |
| tail + 4322664 | 2.646249705 | 0.003050592 |
| tail + 4122384 | 2.764588114 | 0.002498295 |
| tail + 4633 + − 4 | 3.047338974 | 0.001550212 |
| tail + 4322324 | 3.332736672 | 0.000957632 |
| tail − 4322324 | 3.577952269 | 0.00063308 |
| tail + 4332324 | 3.814284708 | 0.000424845 |
| tail + 46 + 31 + 4 | 4.205939866 | 0.000219357 |
| tail + 4223384 | 4.343890786 | 0.000173795 |
| tail + 4631344 | 4.732915799 | 9.01E−05 |
| tail + 4122324 | 4.90405064 | 6.75E−05 |
| tail + 46 + 1144 | 5.409047094 | 2.88E−05 |
| tail + 4222324 | 8.681163162 | 1.15E−07 |
| tail − 1322324 | 10.27372481 | 7.83E−09 |
| tail + 1122324 | 10.89370262 | 2.75E−09 |
| tail + 42 + 1324 | 11.11129754 | 1.90E−09 |
| tail − 1322124 | 11.50748954 | 9.75E−10 |
| tail + 4112384 | →tail + 4633 + 14 | |
| tail + 4633 + 14 | →tail + 4633 + 14 | |
| tail + 4623 + 14 | →tail + 4633 + 14 | |
| tail + 4123384 | →tail + 4633 + 14 | |
| tail + 4133 + 14 | →tail + 4633 + 14 | |
| tail + 4623 + 14 | →tail + 4633 + 14 | |
| tail + 4323 − 14 | →tail + 4333 − 14 | |
| tail + 4333 + 14 | →tail + 4333 − 14 | |
| tail − 46 + 12 − 4 | →tail − 46 + 13 + 4 | |
| tail + 4321324 | →tail + 46 + 13 + 4 | |
| tail + 43 + 13 + 4 | →tail + 46 + 13 + 4 | |
| tail + 46413 + 4 | →tail + 46 + 13 + 4 | |
| tail + 46 + 12 + 4 | →tail + 46 + 13 + 4 | |
| tail + 43 + 13 + 4 | →tail + 46 + 13 + 4 | |
| tail + 41 + 13 + 4 | →tail + 46 + 13 + 4 | |
| tail + 4631 + 14 | →tail + 46 + 1414 | |
| tail + 4121384 | →tail + 46 + 1414 | |
| tail + 46 + 1314 | →tail + 46 + 1414 | |
| tail + 4322314 | →tail + 4322334 | |
| tail + 4322384 | →tail + 4322664 | |
| tail + 4332664 | →tail + 4322664 | |
| tail + 4342664 | →tail + 4322664 | |
| tail + 4322334 | →tail + 4322664 | |

TABLE 3-continued

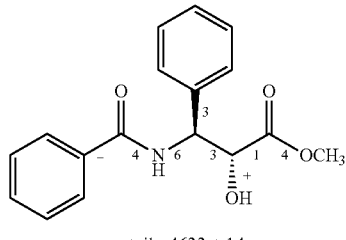

(III)

tail − 4633 + 14

Encoded conformational notations and analysis results for paclitaxel tail methyl ester

| Conformation | ΔG (kcal mol$^{-1}$) | Abundance ratio |
|---|---|---|
| tail + 4322 + 14 | →tail + 4322664 | |
| tail − 4122384 | →tail + 4122384 | |
| tail + 4632 + 14 | →tail + 4122384 | |
| tail + 4132384 | →tail + 4122384 | |
| tail + 4122384 | →tail + 4122384 | |
| tail − 4122384 | →tail + 4122384 | |
| tail + 4122274 | →tail + 4122384 | |
| tail + 4322224 | →tail + 4122384 | |
| tail − 4122274 | →tail + 4122384 | |
| tail + 4633 + 44 | →tail + 4633 + − 4 | |
| tail + 4633 − 44 | →tail + 4633 + − 4 | |
| tail + 4312324 | →tail + 4322324 | |
| tail + 4322124 | →tail + 4322324 | |
| tail + 4222124 | →tail + 4322324 | |
| tail + 4633144 | →tail + 46 + 31 + 4 | |
| tail + 4233 + 14 | →tail + 4223384 | |
| tail + 4433 + 14 | →tail + 4223384 | |
| tail + 46313 + 4 | →tail + 4631344 | |
| tail + 46313 + 4 | →tail + 4631344 | |
| tail + 46 + 23 + 4 | →tail + 4122324 | |
| tail + 46 + 11 + 4 | →tail + 46 + 1144 | |
| tail + 1322324 | →tail + 1122324 | |
| tail + 42 + 13 + 4 | →tail + 42 + 1324 | |

Example 4

Figure 9:
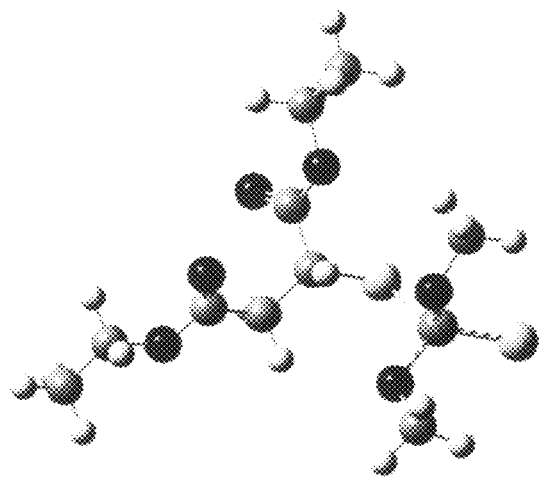
FIG. 9 It is a view showing a molecular model of a conformation represented by PS2211Etsu13111.

A definition of a conformational notation was made by putting a code indicating a dihedral angle to each chemical binding site of (+)-malathion represented by the following chemical structural formula (IV). Subsequently, a definition of a notation uniquely indicating a conformation was made by leaving a notation of a chemical bond of interest and omitting an unnecessary notation. Based on this definition, a notation expressed in only extracted codes was determined. Subsequently, with respect to a molecular model based on the encoded conformational notation, geometry optimization and frequency calculation by a density functional method using the B3LYP functional were performed and an energy value of the resulting geometry optimized structure and a rotatory strength value for each vibration mode in an infrared region were obtained. A homology analysis was performed using the encoded conformational notation, and PS2211Etsu13111 which is a conformational structure having a large abundance ratio was extracted. The encoded conformational notations and the results of the homology analysis are shown in Table 4. A molecular model of a conformation represented by PS2211Etsu13111 is shown in FIG. 9.

TABLE 4

(IV)

CH₃O, S  
   \\ //  
    P  H  
   / \\  |  
CH₃O   S—C—CO—O—CH₂CH₃  
        |  
       CH₂—CO—O—CH₂CH₃

PS2211Etsu13111

Encoded conformational notations and analysis results for (+)-malathion (IV)

| Conformation | ΔG (kcal mol⁻¹) | Abundance ratio |
|---|---|---|
| PS2211Etsu12111 | 0.82205178 | 0.068564695 |
| PS2211Etsu13111 | 0 | 0.274570187 |
| PS2212Etsu13111 | 1.787522288 | 0.013440757 |
| PS2213Etsu13111 | 2.126018501 | 0.007591203 |
| PS2221Etsu12111 | 1.586508119 | 0.018869674 |
| PS2221Etsu13111 | 0.598080848 | 0.100061777 |
| PS2222Etsu13111 | 0.847801088 | 0.065648779 |
| PS2223Etsu13111 | 2.339060844 | 0.005298506 |
| PS32 + 3Etsu13111 | 5.217234355 | 4.12E−05 |
| PS3211Etsu12111 | 0.764592195 | 0.075547074 |
| PS3211Etsu13111 | 0.89823438 | 0.060292006 |
| PS3212Etsu13111 | 2.217408179 | 0.006506137 |
| PS32l3Etsu13111 | 2.582755608 | 0.003511789 |
| PS3221Etsu13111 | 0.814442029 | 0.069450983 |
| PS3222Etsu12111 | 1.019478474 | 0.04913483 |
| PS3311Etsu12111 | 2.542331727 | 0.003759747 |
| PS3311Etsu13111 | 1.008013678 | 0.05009484 |
| PS3312Etsu12111 | 2.442007938 | 0.00445343 |
| PS3313Etsu13111 | 2.31712253 | 0.00549837 |
| PS3 − 32Etsu12111 | 3.935349208 | 0.000358175 |
| PS3331Etsu12111 | 1.625183003 | 0.017677312 |
| PS3331Etsu13111 | 0.613552044 | 0.097482809 |
| PS3 − 33Etsu13111 | 2.874640315 | 0.002145759 |

Subsequently, using the rotatory strength value for each vibration mode in an infrared region, a predicted spectrum of each conformation was obtained. A Gibbs free energy value of a geometry optimized structure was converted into a Boltzmann population, and then, a value obtained by multiplying the predicted spectrum of each conformation by a Boltzmann population factor was added thereto, whereby an average predicted spectrum was obtained.

Figure 10:
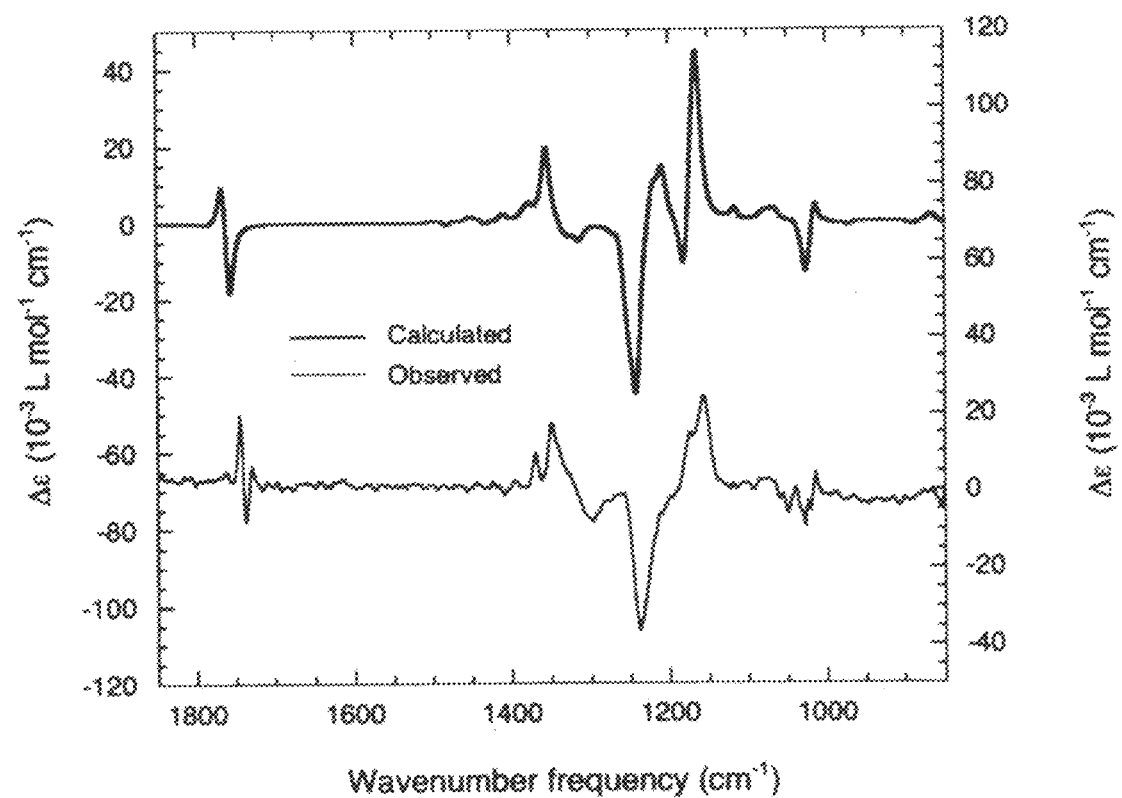
FIG. 10 It is a view showing observed and predicted average vibrational circular dichroism spectra of (+)-malathion (IV).

On the other hand, (+)-malathion (IV) was dissolved in carbon tetrachloride to a final concentration of 0.11 M, and the resulting solution was placed in a BaF₂ window plate sample cell. Then, accumulation was performed for 4 hours and an vibrational circular dichroism spectrum (VCD) and an infrared absorption spectrum (IR) were collected. When the observed vibrational circular dichroism spectrum was compared with the average predicted spectrum, a very good agreement was obtained. From this result, it was verified that the absolute configuration of (+)-malathion is (R)-malathion and a conformation represented by PS2211Etsu13111 is contained in the conformation having a large abundance ratio in carbon tetrachloride. A chart comparing the observed vibrational circular dichroism spectrum with the average predicted spectrum is shown in FIG. 10.

Example 5

Figure 11:
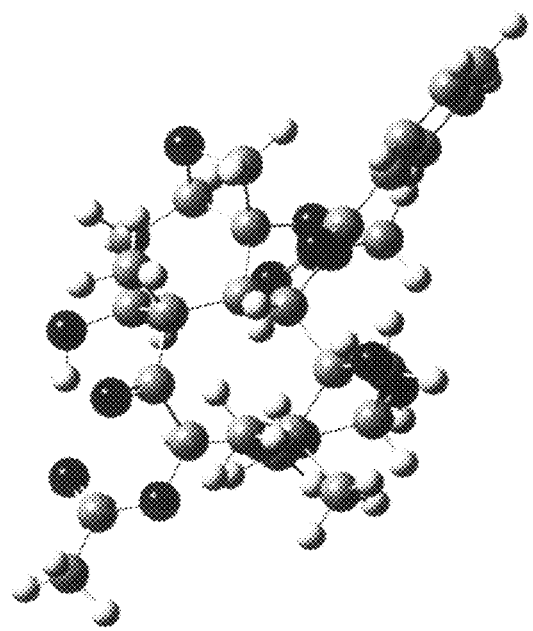
FIG. 11 It is a view showing a molecular model of a conformation represented by bacc233323.

A definition of a conformational notation was made by putting a code indicating a dihedral angle to each chemical binding site of baccatin III which forms a skeleton of paclitaxel and is represented by the following chemical structural formula (V). Subsequently, a definition of a notation uniquely indicating a conformation was made by leaving a notation of a chemical bond of interest and omitting an unnecessary notation. Based on this definition, a notation expressed in only extracted codes was determined. Subsequently, with respect to a molecular model based on the encoded conformational notation, geometry optimization and frequency calculation by a density functional method using the B3LYP functional were performed and an energy value of the resulting geometry optimized structure and a rotatory strength value for each vibration mode in an infrared region were obtained. A homology analysis was performed using the encoded conformational notation, and bacc233323 which is a conformational structure having a large abundance ratio was extracted. The encoded conformational notations and the results of the homology analysis are shown in Table 5. A molecular model of a conformation represented by bacc233323 is shown in FIG. 11.

TABLE 5

(V)

bacc233323

Encoded conformational notations and analysis results for baccatin III (V)

| Conformation | ΔG (kcal mol⁻¹) | Abundance ratio |
|---|---|---|
| bacc233323 | 0 | 0.419233748 |
| bacc233322 | 0.017002007 | 0.407374645 |
| bacc233321 | 0.615863352 | 0.148264348 |
| bacc363323 | 1.982584399 | 0.014765518 |
| bacc233253 | 2.270017299 | 0.009090008 |
| bacc163323 | 3.495929307 | 0.00114812 |
| bacc232323 | 4.81665682 | 0.00012357 |
| bacc233333 | 9.949342925 | 2.14E−08 |
| bacc233233 | 10.45558969 | 9.09E−09 |
| bacc323323 | 10.66435838 | 6.39E−09 |
| bacc223322 | 10.91648801 | 4.18E−09 |
| bacc233133 | 11.88314727 | 8.17E−10 |
| bacc223323 | 13.33759064 | 7.02E−11 |
| bacc133323 | →bacc163323 | |
| bacc213323 | →bacc233323 | |
| bacc-231323 | →bacc232323 | |
| bacc233113 | →bacc233323 | |
| bacc233123 | →bacc233323 | |
| bacc233213 | →bacc233253 | |
| bacc233223 | →bacc233253 | |
| bacc233313 | →bacc233323 | |
| bacc333323 | →bacc363323 | |

Subsequently, using the rotatory strength value for each vibration mode in an infrared region, a predicted spectrum of each conformation was obtained. A Gibbs free energy value of a geometry optimized structure was converted into a Boltzmann population, and then, a value obtained by multiplying the predicted spectrum of each conformation by a Boltzmann population factor was added thereto, whereby an average predicted spectrum was obtained.

Figure 12:
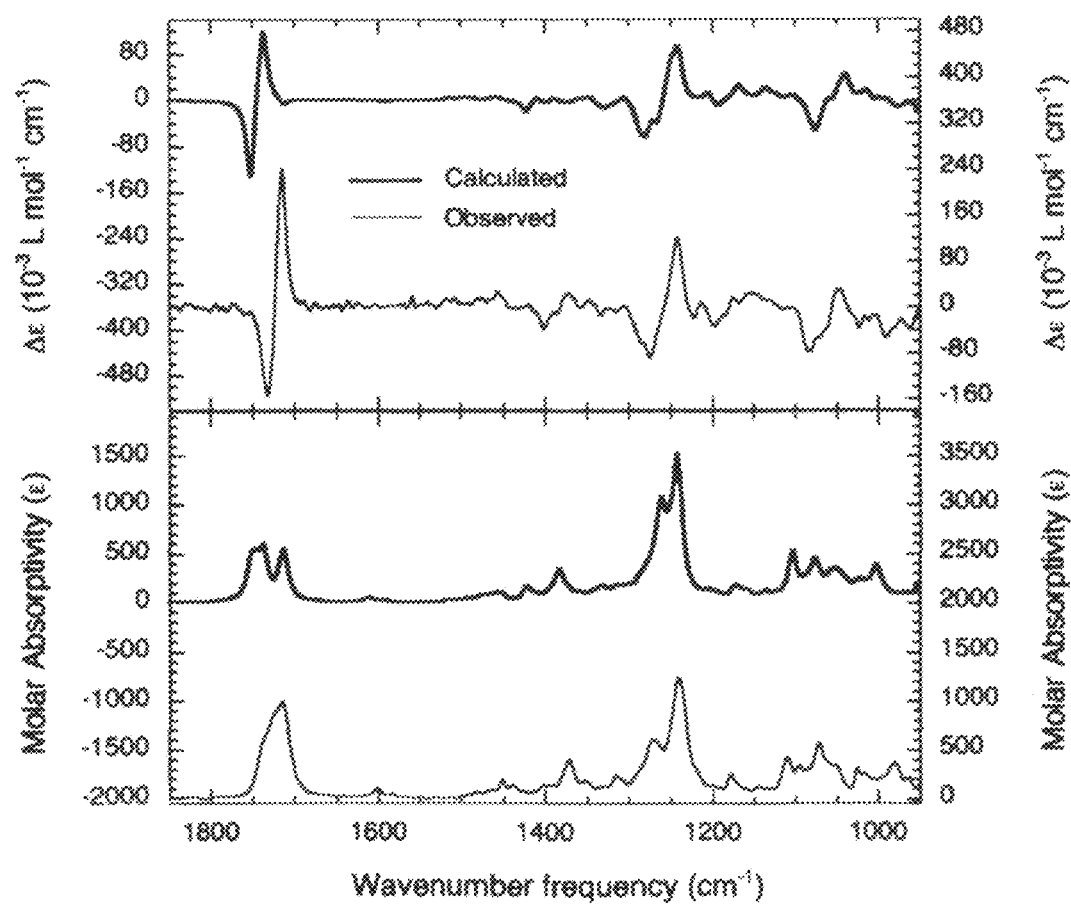
FIG. 12 It is a view showing observed and predicted average vibrational circular dichroism spectra of baccatin III (V) along with infrared spectra thereof.

On the other hand, baccatin III (V) was dissolved in deuterated chloroform to a final concentration of 0.029 M, and the resulting solution was placed in a BaF$_2$ window plate sample cell. Then, accumulation was performed for 4 hours and an vibrational circular dichroism spectrum (VCD) and an infrared absorption spectrum (IR) were collected. When the observed vibrational circular dichroism spectrum was compared with the average predicted spectrum, a very good agreement was obtained. From this result, it was verified that a conformation represented by bacc233323 having a hydrogen bond in the molecule is contained in the conformation having a large abundance ratio in deuterated chloroform. A chart comparing the observed vibrational circular dichroism spectrum with the average predicted spectrum is shown in FIG. 12 along with the infrared spectra.

Further, a structural homology with paclitaxel bound to a protein called β-tubulin which constitutes microtubules was verified using an encoded conformational notation. As a result, in a free solution state, a structural similarity with an unstable conformation represented by bacc233253 was found. From this result, it was suggested that a substituent involved in a hydrogen bond in the molecule serves as an on-off switch and plays an important role in metabolism of paclitaxel.

Example 6

A definition [levo-A-BC(pipa-ab)] of a conformational notation uniquely determining a conformation was made by putting a code predetermined based on a dihedral angle to each chemical binding site with respect to a molecular model of levofloxacin represented by the following chemical structural formula (VI), and an encoded conformational notation was extracted. Subsequently, with respect to the molecular model based on the encoded conformational notation, geometry optimization and frequency calculation by a density functional method using the B3LYP functional were performed and an energy value of the resulting geometry optimized structure was obtained. As for a molecular model in which a structural change occurred as a result of the geometry optimization, by putting a code predetermined based on a dihedral angle to each chemical binding site according to the molecular model once again, an encoded conformational notation was extracted based on the definition of the conformational notation uniquely determining the conformation. It was found that in order to uniquely determine a conformation, it is necessary to express each chemical binding site in a conformational notation using two types of codes determined by dividing 360 degrees into six segments, putting predetermined codes to the respective divided segments, further dividing the respective divided segments into two segments and putting other predetermined codes to the respective further divided segments.

Figure 17:
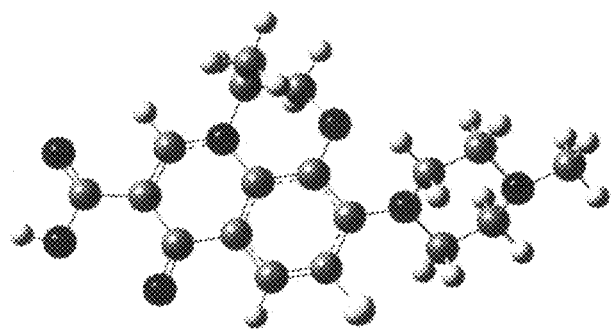
FIG. 17 It is a view showing a molecular model of a conformation represented by levo-2-15(pipa-11β).

As for the dihedral angles for the piperazine ring in levofloxacin (VI), the dihedral angles for the ligand had the same absolute value but opposite signs because the piperazine ring itself is symmetric. Therefore, because it can be expressed in two types of encoded conformational notations, by adopting the predetermined priority rule, an encoded conformational notation was extracted. Subsequently, a homology analysis of the physical property value of the geometry optimized structure was performed using the encoded conformational notation, and a conformational structure of levo-2-15(pipa-11β) which is energetically stable was extracted. The encoded conformational notations and the results of the homology analysis are shown in Table 6. A molecular model of a conformation represented by levo-2-15(pipa-11β) is shown in FIG. 17. The above-mentioned analysis results were outputted from the conformational notation device and displayed.

TABLE 6

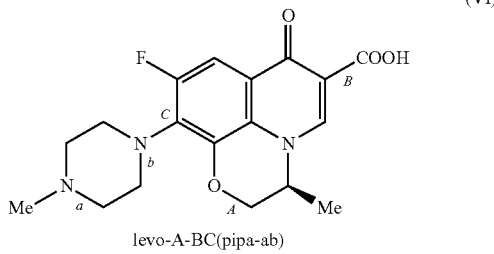

levo-A-BC(pipa-ab)

Encoded conformational notations and analysis results for levofloxacin (VI)

| Conformation | ΔG (kcal mol$^{-1}$) | Abundance ratio |
|---|---|---|
| levo-2-15(pipa-11β) | 0 | 0.282860406 |
| levo-2-12(pipa-11β) | 0.060831635 | 0.25526037 |
| levo-2-13(pipa-11β) | 0.166731352 | 0.213481544 |
| levo-2-16(pipa-11β) | 0.301995149 | 0.16990799 |
| levo-3-15(pipa-11β) | 1.404417895 | 0.026433389 |
| levo-2-45(pipa-11β) | 1.715766645 | 0.01562926 |
| levo-2-42(pipa-11β) | 1.792513565 | 0.013730425 |
| levo-2-43(pipa-11β) | 1.854001764 | 0.012376959 |
| levo-2-46(pipa-11β) | 2.016501189 | 0.009408147 |
| levo-3-42(pipa-11β) | 3.42396646 | 0.000874684 |
| levo-2-42(pipa-2α1β) | 5.300798481 | 3.68E−05 |
| levo-2-3b5(pipa-11β) | →levo-2-15(pipa-11β) | |
| levo-2-41(pipa-11β) | →levo-2-45(pipa-11β) | |
| levo-2-5b5(pipa-11β) | →levo-2-45(pipa-11β) | |
| levo-2-42(pipa-15β) | →levo-2-45(pipa-11β) | |
| levo-2-44(pipa-11β) | →levo-2-43(pipa-11β) | |
| levo-2-42(pipa-21β) | →levo-2-42(pipa-2α1β) | |

Example 7

A definition [ibu-AB(ph-CD)] of a conformational notation uniquely determining a conformation was made by putting a code predetermined based on a dihedral angle to each chemical binding site with respect to a molecular model of (S)-ibuprofen represented by the following chemical structural formula (VII), and an encoded conformational notation was extracted. Subsequently, with respect to the molecular model based on the encoded conformational notation, geometry optimization and frequency calculation by a density functional method using the B3LYP functional were performed and an energy value of the resulting geometry optimized structure was obtained. As for a molecular model in which a structural change occurred as a result of the geometry optimization, by putting a code predetermined based on a dihedral angle to each chemical binding site according to the molecular model once again, an encoded conformational notation was extracted based on the definition of the conformational notation uniquely determining the conformation. It was found that in order to uniquely determine a conformation, it is necessary to express each chemical binding site in a conformational notation using two types of codes determined by dividing 360 degrees into six segments, putting predetermined codes to the respective divided segments, further dividing the respective divided segments into two segments and putting other predetermined codes to the respective further divided segments.

Figure 18:
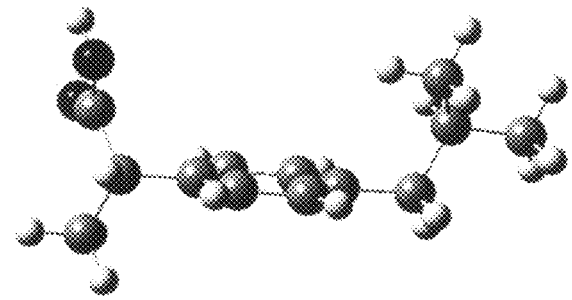
FIG. 18 It is a view showing a molecular model of a conformation represented by ibu-32ασ(ph-3σ5β).

In the case where a dihedral angle was determined in an aromatic ring bound to a propionate moiety in (S)-ibuprofen (VII), which corresponds to the case (3) where a ligand which provides the smallest torsion angle is selected when all ligands are the same, there were two types of conformational structures represented by the same notation. Therefore, by employing a relative positional relation between bonds of interest, discrimination was made using codes of ρ (cis) and τ (trans), whereby an encoded conformational notation was extracted. Subsequently, when a homology analysis of the physical property value of the geometry optimized structure was performed using the encoded conformational notation, it was found that in the case of (S)-ibuprofen (VII) which is a monomer, an vibrational circular dichroism band obtained by calculation is greatly changed depending on a positional relation of a substituent around the aromatic ring bound to the propionate moiety, and these fragments have a strong effect. Further, a conformational structure of ibu-32ασ(ph-3σ5β) which is energetically stable was extracted. The encoded conformational notations and the results of the homology analysis are shown in Table 7. A molecular model of a conformation represented by ibu-32α∝(ph-3σ5β) is shown in FIG. 18. The analysis results were outputted from the conformational notation device and displayed.

TABLE 7

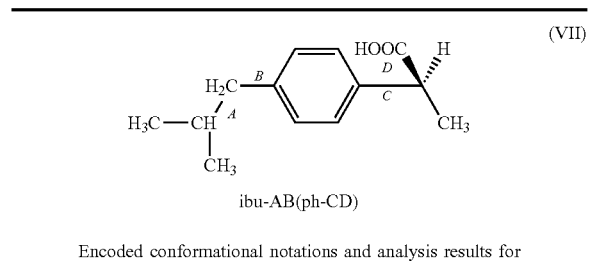

ibu-AB(ph-CD)

Encoded conformational notations and analysis results for (S)-ibuprofen (VII)

| Conformation | ΔG (kcal mol$^{-1}$) | Abundance ratio |
|---|---|---|
| ibu__32ασ(ph__3σ5β) | 0 | 0.248241358 |
| ibu__32ατ(ph__3τ5β) | 0.00825458 | 0.244806894 |
| ibu__23βτ(ph__3τ5β) | 0.128749113 | 0.199757356 |
| ibu__23βσ(ph__3σ5β) | 0.229216978 | 0.168601407 |
| ibu__32ασ(ph__3σ6β) | 1.053911516 | 0.041915173 |
| ibu__23βσ(ph__3σ6α) | 1.212738627 | 0.032059234 |
| ibu__32ατ(ph__3τ6α) | 1.24130991 | 0.030549969 |
| ibu__15βσ(ph__3σ5β) | 1.594380734 | 0.016835059 |
| ibu__15βτ(ph__3τ5β) | 1.658632549 | 0.015104937 |
| ibu__15βσ(ph__3σ6α) | 2.819666423 | 0.002128613 |
| ibu__32ασ(ph__3σ2) | →ibu__32ασ(ph__3σ5β) | |
| ibu__32ασ(ph__3σ1) | →ibu__32ασ(ph__3σ5β) | |
| ibu__32ασ(ph__4σ5β) | →ibu__32ατ(ph__3τ5β) | |
| ibu__32ατ(ph__2τ5β) | →ibu__32ατ(ph__3τ5β) | |
| ibu__24σ(ph__3σ5β) | →ibu__23βτ(ph__3τ5β) | |
| ibu__22τ(ph__3τ5β) | →ibu__23βτ(ph__3τ5β) | |
| ibu__24τ(ph__3τ5β) | →ibu__23βσ(ph__3σ5β) | |
| ibu__22ασ(ph__3σ6α) | →ibu__23βσ(ph__3σ6α) | |

TABLE 7-continued

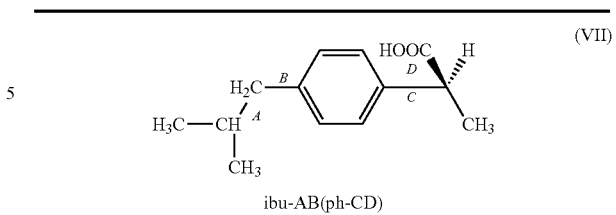

ibu-AB(ph-CD)

Encoded conformational notations and analysis results for (S)-ibuprofen (VII)

| Conformation | ΔG (kcal mol$^{-1}$) | Abundance ratio |
|---|---|---|
| ibu__34σ(ph__3σ6α) | →ibu__32ατ(ph__3τ6α) | |
| ibu__33τ(ph__3τ6α) | →ibu__32ατ(ph__3τ6α) | |
| ibu__32ατ(ph__4τ6α) | →ibu__32ατ(ph__3τ6α) | |
| ibu__12ασ(ph__3σ6α) | →ibu__15βσ(ph__3σ6α) | |

Example 8

A definition [ibu-ABCD(ibu-A'B'C'D')] of a conformational notation uniquely determining a conformation was made by putting a code predetermined based on a dihedral angle to each chemical binding site with respect to a molecular model of (S)-ibuprofen dimer represented by the following chemical structural formula (VIII), and an encoded conformational notation was extracted. Subsequently, with respect to the molecular model based on the encoded conformational notation, geometry optimization and frequency calculation by a density functional method using the B3LYP functional were performed and an energy value of the resulting geometry optimized structure was obtained. As for a molecular model in which a structural change occurred as a result of the geometry optimization, by putting a code predetermined based on a dihedral angle to each chemical binding site according to the molecular model once again, an encoded conformational notation was extracted based on the definition of the conformational notation uniquely determining the conformation. It was found that in order to uniquely determine a conformation, it is necessary to express each chemical binding site in a conformational notation using two types of codes determined by dividing 360 degrees into six segments, putting predetermined codes to the respective divided segments, further dividing the respective divided segments into two segments and putting other predetermined codes to the respective further divided segments.

Figure 19:
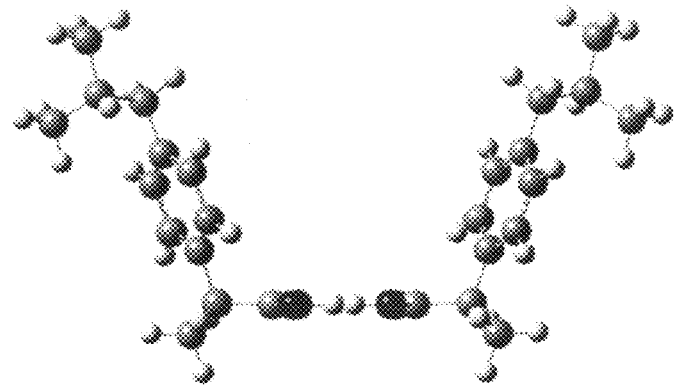
FIG. 19 It is a view showing a molecular model of a conformation represented by ibu-23βτ3τ5β(ibu-23βτ3τ5β).

In the case where a dihedral angle was determined in an aromatic ring bound to a propionate moiety in (S)-ibuprofen dimer (VIII), which corresponds to the case (3) where a ligand which provides the smallest torsion angle is selected when all ligands are the same, there were two types of conformational structures represented by the same notation. Therefore, by employing a relative positional relation between bonds of interest, discrimination was made using codes of ρ (cis) and τ (trans), whereby an encoded conformational notation was extracted. Subsequently, when a homology analysis of the physical property value of the geometry optimized structure was performed using the encoded conformational notation, it was found that in the case of (S)-ibuprofen dimer (VIII), an vibrational circular dichroism band obtained by calculation is greatly changed depending on a positional relation of a substituent around the aromatic ring bound to the propionate moiety, and these fragments have a strong effect. Further, a conformational structure of ibu-23βτ3τ5β(ibu-23βτ3τ5β) which is energetically stable was extracted. The encoded conformational notations and the results of the homology analysis are shown in Table 8. A molecular model of a conformation represented by ibu-23βτ3τ5β(ibu-23βτ3τ5β) is shown in FIG. 19.

TABLE 8

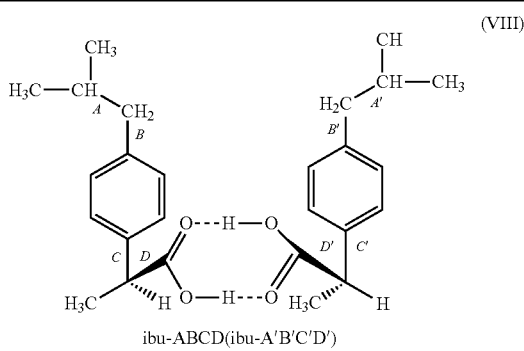

ibu-ABCD(ibu-A'B'C'D')

Encoded conformational notations and analysis results for (S)-ibuprofen dimer (VIII)

| Conformation | ΔG (kcal mol⁻¹) | Abundance ratio |
|---|---|---|
| ibu23βτ3τ5β(ibu23βτ3τ5β) | 0 | 0.114144698 |
| ibu32αο3ο5β(ibu23βο3ο5β) | 0.061554464 | 0.102881468 |
| ibu32αο3ο5β(ibu32αο3ο5β) | 0.11121002 | 0.09461071 |
| ibu23βο3τ6α(ibu23βο3ο5β) | 0.157349701 | 0.087522667 |
| ibu23βτ3τ5β(ibu23βο3ο5β) | 0.312660936 | 0.067340992 |
| ibu32αο3ο5β(ibu23βτ3τ5β) | 0.429109536 | 0.055325362 |
| ibu32ατ3τ6α(ibu32ατ3τ5β) | 0.495496203 | 0.049461096 |
| ibu23βο3ο5β(ibu23βο3ο5β) | 0.508205602 | 0.04841143 |
| ibu32ατ3τ5β(ibu23βτ3τ5β) | 0.52697336 | 0.046902004 |
| ibu32ατ3τ5β(ibu23βο3ο5β) | 0.651034032 | 0.03804141 |
| ibu32αο3ο6α(ibu23βο3ο5β) | 0.757498822 | 0.031784791 |
| ibu32ατ3τ5β(ibu32αο3ο5β) | 0.833495366 | 0.027958568 |
| ibu32ατ3τ5β(ibu32ατ3τ5β) | 0.887672069 | 0.025515503 |
| ibu23βο3τ6α(ibu32αο3ο5β) | 0.905937379 | 0.024740923 |
| ibu32αο3ο6α(ibu23βτ3τ5β) | 0.908692838 | 0.024626131 |
| ibu23βτ3τ6α(ibu32αο3ο5β) | 0.958589547 | 0.022637193 |
| ibu23βτ3τ6α(ibu23βτ3τ5β) | 1.000504893 | 0.021091098 |
| ibu23βο3ο6α(ibu23βτ3τ5β) | 1.019079189 | 0.020440169 |
| ibu23βτ3τ6α(ibu32ατ3τ5β) | 1.067690883 | 0.018830106 |
| ibu23βτ3τ6α(ibu23βο3ο5β) | 1.129406491 | 0.01696743 |
| ibu32ατ3τ6α(ibu23βτ3τ5β) | 1.2143507 | 0.014701211 |
| ibu32αο3ο6α(ibu32αο3ο5β) | 1.227824532 | 0.014370669 |
| ibu23βο3ο6α(ibu32ατ3τ5β) | 1.463201651 | 0.009659369 |
| ibu32ατ3τ6α(ibu32αο3ο5β) | 1.590766213 | 0.007788353 |
| ibu32αο3ο6α(ibu32βτ3τ5β) | 1.599896672 | 0.007669254 |
| ibu32ατ3τ6α(ibu23βο3ο5β) | 1.690893341 | 0.006577393 |

Subsequently, using a rotatory strength value for each vibration mode in an infrared region, a predicted spectrum of each conformation was obtained. Since there were a plurality of conformational structures having a large abundance ratio in a liquid phase, 16 conformational structures having 1 kcal/mol or less were extracted from the most stable conformational structures using the calculation results accompanied by the encoded conformational notations. With respect to the 16 conformational structures, an average predicted spectrum was obtained by converting a Gibbs free energy value of a geometry optimized structure into a Boltzmann population, then adding a value obtained by multiplying the predicted spectrum of each conformation by a Boltzmann population factor thereto.

Figure 20:
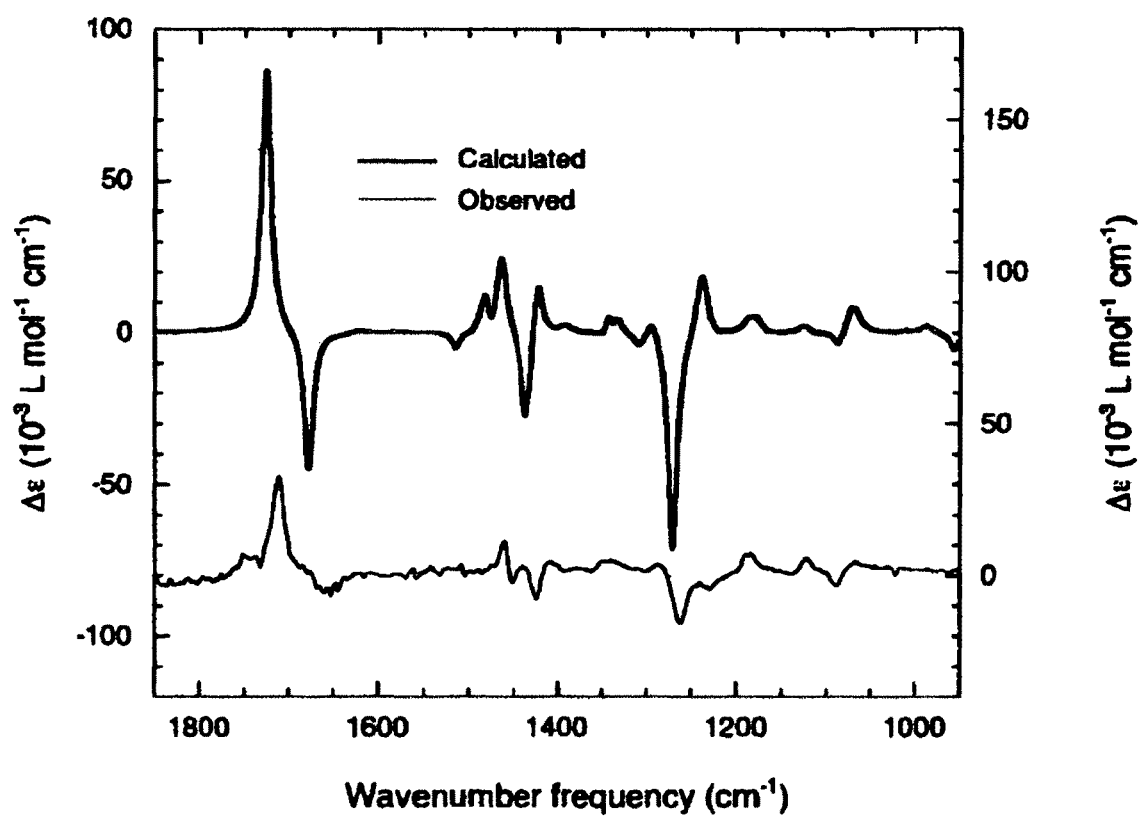
FIG. 20 It is a view showing observed and predicted average vibrational circular dichroism spectra of (S)-ibuprofen dimer (VIII).

On the other hand, (S)-ibuprofen dimer (VIII) was dissolved in deuterated chloroform to a final concentration of 0.11 M, and the resulting solution was placed in a BaF₂ window plate sample cell. Then, accumulation was performed for 4 hours and an vibrational circular dichroism spectrum (VCD) and an infrared absorption spectrum (IR) were collected. When the observed vibrational circular dichroism spectrum was compared with the average predicted spectrum, a very good agreement was obtained. From this result, it was verified that a conformation represented by ibu-23βτ3τ5β(ibu-23βτ3τ5β) having a hydrogen bond is contained in the conformation having a large abundance ratio in deuterated chloroform. A chart comparing the observed vibrational circular dichroism spectrum with the average predicted spectrum is shown in FIG. 20. Further, from a detailed analysis of the spectrum, it was suggested that there are a number of conformational structures other than the 16 conformations although the abundance ratios thereof, for example, contribution of (S)-ibuprofen monomer and the like are not so high, and the band intensity in the observed spectrum is smaller than the predicted value. The above-mentioned analysis results were outputted from the conformational notation device and displayed.

As explained above, the conformation analysis technique according to the present invention is capable of simply analyzing conformations of active species related to drug actions and the like by encoding positions of chemical bonds and dihedral angles therefor thereby notating conformations using simplified symbols in place of a conventional method for notating molecular conformations by an orthogonal coordinate system or ZMATRIX even for conformations. Therefore, the technique can be utilized in, for example, novel drug designing which has been performed with reference to conformations of active species of Taxol, and the like, and exploitation of application thereof such as evaluation of an effect of a hazardous substance on the human body utilizing a structure-activity relationship or the like, or drug discovery based on a pharmacological proteomic approach is sufficiently expected.

Also, in the notation device according to the present invention, encoding of a dihedral angle and the like are more precisely defined than the rule in accordance with the IUPAC Nomenclature, and therefore, a conformation can be uniquely determined, a given molecule can be processed in a unified manner, and large-scale computer processing can be performed. Due to this, a structural change in a conformation related to a drug action or the like can be simply notated, and thus, the device can be utilized in, for example, novel drug designing which has been performed with reference to conformations of active species of levofloxacin, and exploitation of application thereof such as evaluation of an effect of a hazardous substance on the human body utilizing a structure-activity relationship or the like, or drug discovery using a pharmacological proteomic approach is sufficiently expected.

What is claimed is:

1. A conformational notation method comprising:
   receiving, using a processor, a plurality of molecular models as an input, each of the plurality of molecular models corresponding to a different conformation of interest of a compound;
   defining, using the processor, a conformational notation for each molecular model from among the plurality of molecular models;
   storing, in a database, each defined conformational notation by linking the conformational notation to the corresponding molecular model from among the plurality of molecular models; and
   performing, using the processor, conformation analysis for each of the stored conformational notations, wherein the defining the conformational notation for each molecular model includes
  (i) separating the molecular model into one or more fragments,
  (ii) determining a dihedral angle in accordance with an order of a position number determined by the IUPAC Nomenclature and a selection of a substituent group or an atom taking first priority in accordance with the priority rule of the IUPAC Nomenclature in each chemical binding site,
  (iii) assigning, as a classification of the dihedral angle, one of a plurality of codes corresponding to six segments obtained by dividing 360 degrees into the six segments,
  (iv) putting, as the classification of the dihedral angle, one of a plurality of codes corresponding to twelve segments obtained by adding two kinds of codes corresponding to $\alpha$(clockwise) and $\beta$(counterclockwise) to each of the six segments in a case where conformations that should be judged as different from each other belong to a same classification indicated by any one of the plurality of codes corresponding to the six segments in a chemical binding site,
  (v) putting a code corresponding to a chemical bond of interest of the conformational notation or notating by using a notation in which a prefix for correctly indicating only a position of the dihedral angle and the code are combined, and
  (vi) omitting unnecessary notations in a case where a chemical structure is capable of being uniquely determined even if a part of the notations of the chemical bond is omitted when notating a conformation of a fragment,
wherein the conformational notation for each molecular model from among the plurality of molecular models is defined so that each of the conformation notations is unique,
wherein the performing the conformation analysis for each of the stored conformational notations includes
  (i) extracting the conformational notation from the database,
  (ii) creating a molecular model from the extracted conformational notation,
  (iii) performing geometry optimization and frequency calculation for the created molecular model,
  (iv) determining an energy value or another physical property value of the resulting geometry optimized molecular model, and
  (v) storing the determined energy value or the other physical property value in the database by linking the stored value to the corresponding molecular model,
wherein, when the geometry optimization for the molecular model created from the extracted conformational notation requires that the molecular model corresponding to the extracted conformational notation be changed, the defining the conformational notation for the molecular model corresponding to the extracted conformational notation is repeated, and
wherein the conformational notation method further comprises:
  receiving, in a case where an energy value or another physical property is observed for the compound to be analyzed, the observed value is linked to each of the plurality of molecular models corresponding to the compound to be analyzed, the observed energy value or the observed other physical property being obtained using vibration circular dichroism analysis or X-ray crystal structural analysis;
  extracting, from the database, the conformational notation for each molecular model from among the plurality of molecular models;
  performing homology analysis using (i) the received observed energy value or the received observed other physical property and (ii) the extracted conformation notion for each molecular model from among the plurality of molecular models; and
  outputting, to a display, the results of the homology analysis and the extracted conformational notation for each molecular model from among the plurality of molecular models.

2. The conformational notation method according to claim 1, wherein in a case where a conformational notation for a molecular model is able to be linked to a plurality of molecular models according to the priority rule corresponding to "when all of ligand is same, selecting one that torsion angle is smallest" is applied in selecting the most priority substituent group or atom in accordance with the priority rule of the IUPAC Nomenclature, the conformational notation for the molecular model is defined by further notating a code corresponding to $\rho$(cis) or $\tau$(trans) based on a relative position relationship so as to uniquely define the conformational notation for the molecular model.

3. The conformational notation method according to claim 1, wherein in a case where a conformational notation for a molecular model may be one or more conformational notations because the dihedral angle of the ligands are the same and it cannot be determined whether to select the ligands of clockwise or counterclockwise when the priority rule that correspond to "when all of ligand is same, selecting one that torsion angle is smallest" is applied in selecting the most priority substituent group or atom in accordance with the priority rule of the IUPAC Nomenclature, the conformational notation for the molecular model is defined by selecting a conformational notation, from among the one or more conformation notations, according to a priority rule that prioritizes clockwise so as to uniquely define the conformational notation for the molecular model.

4. The conformational notation method according to claim 2, wherein in a case where a conformational notation for a molecular model may be one or more conformational notations because the dihedral angle of the ligands are the same and it cannot be determined whether to select the ligands of clockwise or counterclockwise when the priority rule that correspond to "when all of ligand is same, selecting one that torsion angle is smallest" is applied in selecting the most priority substituent group or atom in accordance with the priority rule of the IUPAC Nomenclature, the conformational notation for the molecular model is defined by selecting a conformational notation, from among the one or more conformational notations, according to a priority rule that prioritizes clockwise so as to uniquely define the conformational notation for the molecular model.

5. A conformational notation device comprising:
  a database; and
  a processor that (i) receives a plurality of molecular models as an input, each of the plurality of molecular models corresponding to a different conformation of interest of a compound, (ii) defines a conformational notation for each molecular model from among the plurality of molecular models, (iii) stores, in the database, each defined conformational notation by linking the conformational notation to the corresponding molecular model from among the plurality of molecular models, and (iv) performs conformation analysis for each of the stored conformational notations, wherein the processor defines the conformational notation for each molecular model by
(i) separating the molecular model into one or more fragments,
(ii) determining a dihedral angle in accordance with an order of a position number determined by the IUPAC Nomenclature and a selection of a substituent group or an atom taking first priority in accordance with the priority rule of the IUPAC Nomenclature in each chemical binding site,
(iii) assigning, as a classification of the dihedral angle, one of a plurality of codes corresponding to six segments obtained by dividing 360 degrees into the six segments,
(iv) putting, as the classification of the dihedral angle, one of a plurality of codes corresponding to twelve segments obtained by adding two kinds of codes corresponding to α(clockwise) and β(counterclockwise) to each of the six segments in a case where conformations that should be judged as different from each other belong to a same classification indicated by any one of the plurality of codes corresponding to the six segments in a chemical binding site,
(v) putting a code corresponding to a chemical bond of interest of the conformational notation or notating by using a notation in which a prefix for correctly indicating only a position of the dihedral angle and the code are combined, and
(vi) omitting unnecessary notations in a case where a chemical structure is capable of being uniquely determined even if a part of the notations of the chemical bond is omitted when notating a conformation of a fragment, wherein the processor defines the conformational notation for each molecular model from among the plurality of molecular models so that each of the conformation notations is unique, wherein the processor performs the conformation analysis for each of the stored conformational notations by
(i) extracting the conformational notation from the database,
(ii) creating a molecular model from the extracted conformational notation,
(iii) performing geometry optimization and frequency calculation for the created molecular model,
(iv) determining an energy value or another physical property value of the resulting geometry optimized molecular model, and
(v) storing the determined energy value or the other physical property value in the database by linking the stored value to the corresponding molecular model, wherein, when the geometry optimization for the molecular model created from the extracted conformational notation requires that the molecular model corresponding to the extracted conformational notation be changed, the processor repeats defining the conformational notation for the molecular model corresponding to the extracted conformational notation, wherein, in a case where an energy value or another physical property is observed for the compound to be analyzed and the observed value is linked to each of the plurality of molecular models corresponding to the compound to be analyzed, the processor stores the observed value in the database by linking the observed value to each of the plurality of molecular models, and wherein the processor (i) receives, in a case where an energy value or another physical property is observed for the compound to be analyzed and the observed value is linked to each of the plurality of molecular models corresponding to the compound to be analyzed, the observed energy value or the observed other physical property being obtained using vibration circular dichroism analysis or X-ray crystal structural analysis, (ii) extracts, from the database, the conformational notation for each molecular model from among the plurality of molecular models, (iii) performs homology analysis using (a) the received observed energy value or the received observed other physical property and (b) the extracted conformation notion for each molecular model from among the plurality of molecular models, and (iv) outputting, to a display, the results of the homology analysis and the extracted conformational notation for each molecular model from among the plurality of molecular models.

6. The conformational notation device according to claim 5, wherein in a case where a conformational notation defined for a molecular model is able to be linked to a plurality of molecular models according to the priority rule corresponding to "when all of ligand is same, selecting one that torsion angle is smallest" is applied in selecting the most priority substituent group or atom in accordance with the priority rule of the IUPAC Nomenclature, the processor further defines the conformational notation for the molecular model by further notating a code corresponding to ρ(cis) or τ(trans) based on a relative position relationship so as to uniquely define the conformational notation for the molecular model.

7. The conformational notation device according to claim 5, wherein in a case where a conformation notation for a molecular model may be one or more conformational notations because the dihedral angle of the ligands are the same and it cannot be determined whether to select the ligands of clockwise or counterclockwise when the priority rule that correspond to "when all of ligand is same, selecting one that torsion angle is smallest" is applied in selecting the most priority substituent group or atom in accordance with the priority rule of the IUPAC Nomenclature, the processor defines the conformational notation for the molecular model by selecting a conformational notation, from among the one or more conformation notations, according to a priority rule that prioritizes clockwise so as to uniquely define the conformational notation for the molecular model.

8. The conformational notation device according to claim 6, wherein in a case where a conformational notation for a molecular model may be one or more conformational notations because the dihedral angle of the ligands are the same and it cannot be determined whether to select the ligands of clockwise or counterclockwise when the priority rule that correspond to "when all of ligand is same, selecting one that torsion angle is smallest" is applied in selecting the most priority substituent group or atom in accordance with the priority rule of the IUPAC Nomenclature, the processor defines the conformational notation for the molecular model by selecting a conformation notation, from among the one or more conformational notations, according to a priority rule that prioritizes clockwise so as to uniquely define the conformational notation for the molecular model.

* * * * *